United States Patent
Kim et al.

(10) Patent No.: US 9,833,593 B2
(45) Date of Patent: Dec. 5, 2017

(54) CATHETER FOR TREATING ECTOPIC PREGNANCY, CATHETER GUIDE, AND CATHETER UNIT FOR TREATING ECTOPIC PREGNANCY, INCLUDING THE CATHETER AND THE CATHETER GUIDE

(75) Inventors: Sun Haeng Kim, Seoul (KR); Young Tae Kim, Seoul (KR); Ki Hoon Ahn, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 895 days.

(21) Appl. No.: 13/982,928

(22) PCT Filed: Nov. 25, 2011

(86) PCT No.: PCT/KR2011/009082
§ 371 (c)(1),
(2), (4) Date: Oct. 8, 2013

(87) PCT Pub. No.: WO2012/105744
PCT Pub. Date: Aug. 9, 2012

(65) Prior Publication Data
US 2014/0031742 A1 Jan. 30, 2014

(30) Foreign Application Priority Data

Jan. 31, 2011 (KR) ................ 10-2011-0009742
Oct. 5, 2011 (KR) ................ 10-2011-0101369
Oct. 21, 2011 (KR) ................ 10-2011-0107882

(51) Int. Cl.
*A61M 25/00* (2006.01)
*A61B 17/42* (2006.01)
*A61M 31/00* (2006.01)
*A61M 25/01* (2006.01)
*A61B 17/00* (2006.01)
*A61B 17/34* (2006.01)
*A61B 17/435* (2006.01)

(52) U.S. Cl.
CPC ......... *A61M 25/0026* (2013.01); *A61B 17/42* (2013.01); *A61M 31/00* (2013.01);
(Continued)

(58) Field of Classification Search
CPC ............ A61M 25/0026; A61M 25/003; A61M 2025/0037; A61B 17/435; A61B 17/42;
(Continued)

(56) References Cited

U.S. PATENT DOCUMENTS 4,846,791 A * 7/1989 Hattler .............. A61M 25/0026
604/158
5,147,315 A * 9/1992 Weber .................... A61B 17/43
600/35
(Continued)

FOREIGN PATENT DOCUMENTS

JP 07-323088 A 12/1995
JP 2004-533864 A 11/2004
(Continued)

*Primary Examiner* — Laura Bouchelle
(74) *Attorney, Agent, or Firm* — Rabin & Berdo, P.C.

(57) ABSTRACT

The present invention relates to a catheter for treating ectopic pregnancy, of which one end is inserted into the fallopian tube through the vaginal cavity, and the other end is exposed to the outside of the body, wherein the catheter comprises: at least one passage portion forming a liquid passage entering through the one end or the other end; a penetrative portion connected to the one end, and including a foremost end for penetrating the gestational sac; and a connecting portion connected to the other end, and capable of being coupled to at least one syringe tool for injecting or suctioning the liquid. Accordingly, side effects from open surgery can be prevented, and excellent treatment effects can be obtained by more safely and quickly treating ectopic pregnancy.

21 Claims, 25 Drawing Sheets

(52) U.S. Cl.
CPC ......... *A61B 17/3478* (2013.01); *A61B 17/435* (2013.01); *A61B 2017/00318* (2013.01); *A61B 2017/00323* (2013.01); *A61B 2017/00867* (2013.01); *A61M 25/007* (2013.01); *A61M 25/0032* (2013.01); *A61M 25/01* (2013.01); *A61M 2025/0031* (2013.01); *A61M 2025/0037* (2013.01)

(58) Field of Classification Search
CPC ...... A61B 17/3478; A61B 2017/00318; A61B 2017/00323
USPC .......................................................... 604/43
See application file for complete search history.

(56) References Cited

U.S. PATENT DOCUMENTS

| | | | |
|---|---|---|---|
| 5,389,089 | A | 2/1995 | Bauer et al. |
| 5,743,258 | A | 4/1998 | Sato et al. |
| 5,935,098 | A | 8/1999 | Blaisdell et al. |
| 9,277,981 | B2 * | 3/2016 | Vazquez Rojas ...... A61D 19/04 |
| 2006/0183973 | A1 | 8/2006 | Kamrava |
| 2006/0264905 | A1 * | 11/2006 | Eskridge ........... A61M 25/0021 604/523 |
| 2007/0185435 | A1 | 8/2007 | Sampson |
| 2007/0197896 | A1 | 8/2007 | Moll et al. |
| 2007/0219529 | A1 | 9/2007 | Abe et al. |
| 2008/0091196 | A1 * | 4/2008 | Deal .................. A61B 18/1477 606/45 |
| 2008/0161757 | A1 * | 7/2008 | Nayak ..................... A61M 5/19 604/82 |
| 2008/0183156 | A1 | 7/2008 | Yoo |
| 2008/0245371 | A1 | 10/2008 | Gruber |
| 2009/0270835 | A1 | 10/2009 | Kushner |
| 2010/0198013 | A1 * | 8/2010 | Binmoeller ........ A61B 1/00091 600/121 |

FOREIGN PATENT DOCUMENTS

| | | |
|---|---|---|
| JP | 3162023 U | 8/2010 |
| KR | 10-1995-0005333 A | 3/1995 |
| KR | 10-2007-0094536 A | 9/2007 |
| KR | 10-2008-0070338 A | 7/2008 |

* cited by examiner

CATHETER FOR TREATING ECTOPIC PREGNANCY, CATHETER GUIDE, AND CATHETER UNIT FOR TREATING ECTOPIC PREGNANCY, INCLUDING THE CATHETER AND THE CATHETER GUIDE

TECHNICAL FIELD

The present invention relates to a catheter for treating ectopic pregnancy, a catheter guide, and a catheter unit including the catheter and the catheter guide.

BACKGROUND ART

In general, an ovum or egg released from an ovary is stably fertilized with a sperm at a tubal ampulla at a position corresponding to ⅓ of the length of the fallopian tube from the ovary, and then is transported into the uterus where implantation occurs to induce the normal pregnancy. However, an ectopic pregnancy or eccyesis occurs in about one in 150 pregnancies. That is, the ectopic pregnancy refers to the implantation of the fertilized egg at abnormal positions. The ectopic pregnancy can occur in various abnormal forms such as tubal pregnancy, cervical pregnancy, ovarian pregnancy, and abdominal pregnancy depending on the position of implantation. Among them, the tubal pregnancy occupies the highest ratio, accounting for approximately 98% of all the ectopic pregnancies. Such ectopic pregnancy has a high risk in that it necessarily involves the abortion of the fetus as well as threatens the health of the mother. In other words, in case of the tubal pregnancy, the rapid growth of the embryo involves tubal rupture, which brings about serious sequelae, making future pregnancy impossible. To this end, conventionally, a medical treatment in which methotrexate, a kind of anticancer drug is injected intramuscularly, and surgical procedures such as laparoscopic surgery and laparotomy were performed. Nevertheless, if the mother does not respond to the drug methotrexate in the medical treatment, the surgical procedures are inevitable. However, such surgical procedures entail the risks including side effects of anesthesia caused by an invasive method, bleeding due to vascular injury, abrupt bowel injury, fascia damage of the abdominal wall, and the like during incision of the abdominal wall.

DISCLOSURE OF INVENTION

Technical Problem

Accordingly, it is an object of the present invention to provide a catheter, a catheter guide and a catheter unit including the catheter and the catheter unit, for treating ectopic pregnancy, which are configured to implement a structure that is non-invasive and stable, and achieve excellent therapeutic effects.

Another object of the present invention is to prevent side effects which may occur due to a surgical resection by enabling a drug to be injected in a gestational sac and to safely and rapidly perform a medical treatment of the ectopic pregnancy.

In addition, another object of the present invention is to treat ectopic pregnancy in a safer and more accurate manner by safely securing a path for entry of a catheter for treating ectopic pregnancy into a fallopian tube through a vaginal cavity using a catheter guide.

Also, another object of the present invention is to more smoothly treat ectopic pregnancy by allowing at least one of a catheter for treating ectopic pregnancy and a catheter guide for treating ectopic pregnancy to be formed as a curved structure having a preset radius of curvature or forming a movable structure through a direction control unit.

In addition, another object of the present invention is to more smoothly treat ectopic pregnancy by allowing a connecting part capable of being connected to a syringe tool (or suction device or injection device) to be formed integrally with a catheter for treating ectopic pregnancy or to be formed as a separate member.

In addition, another object of the present invention is to prevent a body fluid from being introduced into a catheter for treating ectopic pregnancy and a catheter guide for treating ectopic pregnancy when the catheter and the catheter guide enter a female body by closing the front end parts of the catheter and the catheter guide using a thin membrane.

In addition, another object of the present invention is to wholly or partially apply a material capable of being identified by an imaging apparatus on a catheter for treating ectopic pregnancy and a catheter guide for treating ectopic pregnancy, or manufacture the catheter and the catheter guide using such material to grasp a degree of access to the gestational sac.

Technical Solution

To achieve the above objects, in one aspect, the present invention provides a catheter for treating ectopic pregnancy, which is inserted at one end thereof into a fallopian tube through a vaginal cavity and is exposed at the other end thereof to the outside of a female body, wherein the catheter comprises: at least one flow passage part formed in the catheter and having a flow passage along which liquid introduced into the catheter through the one end or the other end of the catheter flows; a penetrating part connected to the one end of the catheter and including a front tip end for penetrating into a gestational sac; and a connecting part connected to the other end of the catheter and configured to be coupled to at least one syringe tool for injecting or suctioning the liquid.

In addition, in the present invention, the syringe tool may include at least one of a drug injection tool configured to inject a drug into the gestational sac and an amniotic fluid suction tool configured to suction an amniotic fluid in the gestational sac.

In addition, in the present invention, the connecting part may include at least one of a first opening portion configured to allow the drug which is to be delivered into the gestational sac to be introduced into the flow passage part from the syringe tool therethrough, a second opening portion configured to allow the amniotic fluid in the gestational sac to be discharged to the syringe tool therethrough.

In addition, in the present invention, the connecting part may include a first connecting part including the first opening portion and a second connecting part including the second opening portion, the first connecting part and the second connecting part being configured to be branched off from each other.

In addition, in the present invention, the connecting part may be configured as a separate member so that it can be engaged with and disengaged from the catheter for treating ectopic pregnancy.

In addition, in the present invention, if the connecting part is configured as the separate member, one end of the connecting part it is detachably connected to a distal end of the catheter for treating ectopic pregnancy so as to allow the one end to fluidically communicate with the flow passage part, and the other end of the connecting part includes a diameter enough to be capable of being connected to the syringe tool.

In addition, in the present invention, the penetrating part may include at least one of a third opening portion configured to allow the drug introduced into the flow passage part from the syringe tool to be discharged to the gestational sac therethrough, and a fourth opening portion configured to allow the amniotic fluid in the gestational sac to be introduced into the flow passage part therethrough.

In addition, in the present invention, the penetrating part may be formed to have an inclined face formed at a predetermined angle, and at least one of the third opening portion and the fourth opening portion is formed on the inclined face.

In addition, in the present invention, the connecting part may further include a direction control unit configured to adjust the progress direction of the catheter for treating ectopic pregnancy.

In another aspect, the present invention provides a catheter guide which is inserted at one end thereof into a fallopian tube through a uterine and is exposed at the other end thereof to the outside of a female body, wherein the catheter guide includes a through-hole forming a path along which a catheter for treating ectopic pregnancy is inserted into a fallopian tube, the through-hole having a preset radius of curvature.

In another aspect, the present invention provides a catheter unit for treating ectopic pregnancy, which includes a catheter for treating ectopic pregnancy and a catheter guide for treating ectopic pregnancy.

In another aspect, the present invention provides a catheter for treating ectopic pregnancy, which is inserted at one end thereof into a fallopian tube through a vaginal cavity and is exposed at the other end thereof to the outside of a female body, wherein the catheter comprises: a penetrating part connected to the one end of the catheter and including a front tip end for penetrating into a gestational sac; a first flow passage part configured to form a flow passage of a drug introduced thereto through the other end of the catheter; and at least one flow passage part formed in the catheter and having a flow passage along which liquid introduced into the catheter through the one end or the other end of the catheter flows; a penetrating part connected to the one end of the catheter and including a front tip end for penetrating into a gestational sac; and a first connecting part connected to the other end of the catheter and configured to be coupled to a drug injection tool for injecting the drug into the gestational sac.

In addition, in the present invention, the catheter for treating ectopic pregnancy may further include: a second flow passage part formed in the catheter and having a flow passage along which the amniotic fluid in the gestational sac, introduced into the catheter through the one end of the catheter flows; and a second connecting part connected to the other end of the catheter and configured to be coupled to an amniotic fluid suction tool for suctioning the amniotic fluid in the gestational sac.

In addition, in the present invention, the first connecting part includes a first opening portion configured to allow the drug discharged from drug injection tool to be introduced into the catheter therethrough so as to be delivered into the gestational sac, the first opening portion being connected to the penetrating part through the first flow passage part.

In addition, in the present invention, the second connecting part may include a second opening portion configured to allow the amniotic fluid in the gestational sac to be discharged to the outside therethrough so as to be introduced into the amniotic fluid suction tool, the second opening portion being connected to the penetrating part through the second flow passage part.

In addition, in the present invention, at least one of the first connecting part and the second connecting part may be configured as a separate member so that it can be engaged with and disengaged from the catheter for treating ectopic pregnancy.

In addition, in the present invention, the penetrating part may be formed to have an inclined face formed at a predetermined angle.

In addition, in the present invention, the penetrating part may include at least one of a third opening portion configured to allow the drug introduced into the first flow passage part from the drug injection tool to be discharged to the gestational sac therethrough, and a fourth opening portion configured to allow the amniotic fluid in the gestational sac to be introduced into the second flow passage part therethrough.

In addition, in the present invention, the catheter for treating ectopic pregnancy and the catheter guide may be coated with or manufactured of a material which can be identified by an imaging apparatus.

In another aspect, the present invention provides a catheter guide for treating ectopic pregnancy, including: a catheter through-part configured to be inserted at one end thereof into a fallopian tube through a vaginal cavity and exposed at the other end thereof to the outside of a female body, the catheter through-part including a through-line through which a catheter for treating ectopic pregnancy can pass; a first opening portion formed at one end of the catheter through-part so that the catheter for treating ectopic pregnancy can exit the first opening portion; a second opening portion formed at the other end of the catheter through-part so that the catheter for treating ectopic pregnancy can enter the second opening portion, wherein the catheter through-part interconnects the first opening portion and the second opening portion, and includes a radius of curvature which is preset along the lengthwise direction thereof.

In another aspect, the present invention provides a catheter unit for treating ectopic pregnancy, including: a catheter guide for treating ectopic pregnancy, which comprises: a catheter through-part configured to be inserted at one end thereof into a fallopian tube through a vaginal cavity and exposed at the other end thereof to the outside of a female body, the catheter through-part comprising a through-line through which a catheter for treating ectopic pregnancy can pass; a first opening portion formed at one end of the catheter through-part so that the catheter for treating ectopic pregnancy can exit the first opening portion; a second opening portion formed at the other end of the catheter through-part so that the catheter for treating ectopic pregnancy can enter the second opening portion, wherein the catheter through-part interconnects the first opening portion and the second opening portion, and includes a radius of curvature which is preset along the lengthwise direction thereof; and a catheter for treating ectopic pregnancy, the catheter being inserted at one end thereof into a fallopian tube through the catheter through-part and being exposed at the other end thereof to the outside of the female body.

In another aspect, the present invention provides a catheter guide for treating ectopic pregnancy, including: a first catheter guide configured to be inserted at one end thereof into a female body through a vaginal cavity and exposed at the other end thereof to the outside of the female body, the first catheter guide having a preset stiffness or rigidity so that the axial line thereof forms a predetermined curved structure along the lengthwise direction of the first catheter guide; and a second catheter guide configured to be movably penetratingly disposed inside the first catheter guide, the second catheter guide being inserted at one thereof into the fallopian tube along first catheter guide and being exposed at the other end thereof to the outside of the female body so that the ectopic pregnancy treatment catheter can be passed through the second catheter guide.

In the catheter guide for treating ectopic pregnancy, the ectopic pregnancy treatment catheter may include: a flow passage part configured to form a flow passage of a liquid; a penetrating part including a front tip end for penetrating into a gestational sac; and a connecting part connected to a syringe tool including at least one of a drug injection tool configured to inject a drug into the gestational sac through the flow passage part and an amniotic fluid suction tool configured to suction an amniotic fluid in the gestational sac through the flow passage part.

In the catheter guide for treating ectopic pregnancy, the second catheter guide may include a surface-processed part formed on the outer peripheral surface thereof so as to prevent adsorption between the outer peripheral surface of the second catheter guide and the inner peripheral surface of the first through-part of the first catheter guide.

In the catheter guide for treating ectopic pregnancy, the surface-processed part may form a recessed pattern.

In the catheter guide for treating ectopic pregnancy, the surface-processed part may form a projected pattern.

In another aspect, the present invention provides a catheter guide for treating ectopic pregnancy, which is configured to be inserted at one end thereof into a female body through a vaginal cavity and exposed at the other end thereof to the outside of the female body so that a catheter for treating ectopic pregnancy can pass through the catheter guide, wherein the catheter guide has a preset stiffness or rigidity so that the axial line thereof forms a predetermined curved structure along the lengthwise direction of the catheter guide.

In another aspect, the present invention provides a catheter unit for treating ectopic pregnancy, including: an ectopic pregnancy treatment catheter guide which includes: a first catheter guide configured to be inserted at one end thereof into a female body through a vaginal cavity and exposed at the other end thereof to the outside of the female body, the first catheter guide having a preset stiffness or rigidity so that the axial line thereof forms a predetermined curved structure along the lengthwise direction of the first catheter guide; and a second catheter guide configured to be movably penetratingly disposed inside the first catheter guide, the second catheter guide being inserted at one thereof into the fallopian tube along first catheter guide and being exposed at the other end thereof to the outside of the female body so that the ectopic pregnancy treatment catheter can be passed through the second catheter guide; and an ectopic pregnancy treatment catheter configured to be inserted at one end thereof into a fallopian tube through the second catheter guide and exposed at the other end thereof to the outside of the female body.

In another aspect, the present invention provides a method for treating ectopic pregnancy, including the steps of: a first catheter guide entry step of inserting one end of the first catheter guide into a female body through a vaginal cavity and exposing the other end of the first catheter guide to the outside of the female body, the first catheter guide having a preset stiffness or rigidity so that the axial line thereof forms a predetermined curved structure along the lengthwise direction of the first catheter guide; a second catheter entry step of inserting one end of the second catheter guide into the first catheter guide through the other end of the first catheter guide along the lengthwise direction of the axial line of the first catheter guide, and allowing the one end of the second catheter guide to enter a fallopian tube; a catheter entry step of allowing a catheter for treating ectopic pregnancy to enter the second catheter guide while passing through the second catheter guide and allowing a penetrating part of the catheter to enter the fallopian tube, the catheter being inserted at one end thereof into a fallopian tube and being exposed at the other end thereof to the outside of the female body, wherein the catheter comprises: at least one flow passage part formed in the catheter and having a flow passage along which liquid introduced into the catheter through the one end or the other end of the catheter flows; the penetrating part connected to the one end of the catheter and including a front tip end for penetrating into a gestational sac; and a connecting part connected to the other end of the catheter and configured to be coupled to at least one syringe tool for injecting or suctioning the liquid; and a penetration step of controlling the ectopic pregnancy treatment catheter to allow the penetrating part of the catheter to penetrate into the gestational sac in the fallopian tube.

The ectopic pregnancy treatment method treatment method according to the present invention may further include an injection step of injecting a liquid into the gestational sac through the syringe tool after the penetration step.

The ectopic pregnancy treatment method treatment method according to the present invention may further include a suction step of suctioning a liquid from the gestational sac through the syringe tool after the penetration step.

The ectopic pregnancy treatment method treatment method according to the present invention may further include a first catheter guide removal step of removing the first catheter guide after the second catheter guide entry step.

The ectopic pregnancy treatment method treatment method according to the present invention may further include a first catheter guide removal step of removing the first catheter guide after the catheter entry step.

Advantageous Effects

The catheter for treating ectopic pregnancy, the catheter guide, and the catheter unit including the catheter and the catheter guide according to the present invention having the same configuration as described above have the following advantageous effects.

First, the present invention enables the catheter to be inserted in vivo through the vaginal cavity and a drug to be injected in a gestational sac, thereby preventing side effects which may occur due to a surgical resection. For example, it is possible to avoid a risk of anesthesia, bleeding due to vascular injury, abrupt bowel injury, fascia damage of the abdominal wall, and the like during incision of the abdominal wall.

Second, the present invention enables paracentesis of the gestational sac and direct infusion of a drug, so that the medical treatment of ectopic pregnancy can be performed safely and promptly.

Third, the present invention enables direction suction of the amniotic fluid from the gestational sac and drug infusion, so that treatment of ectopic pregnancy can be performed in a safe and complete manner.

Fourth, the present invention can safely secure an entry path of the ectopic pregnancy treatment catheter to the uterus and the fallopian tube, so that the treatment of ectopic pregnancy can be performed in a safer and more accurate manner.

Fifth, the present invention enables at least one of the ectopic pregnancy treatment catheter and the catheter guide to be formed as a curved structure having a preset radius of curvature, or implements a movable structure through the direction control unit, so that the treatment of ectopic pregnancy can be performed more smoothly.

Sixth, the present invention enables the connecting part which can be connected to the syringe tool (i.e., suction device or injection device) to be formed integrally with the ectopic pregnancy treatment catheter or formed as a separate member, so that the treatment of ectopic pregnancy can be performed more smoothly.

Seventh, the present invention enables the front end part the ectopic pregnancy treatment catheter guide to be closed by a membrane so that a body fluid can be prevented from being introduced into the catheter and the catheter guide during its in vivo insertion.

Eighth, the present invention implements the ectopic pregnancy treatment catheter guide having a double nested arrangement structure, so that smoother and more rapid measures can be taken during the treatment procedures of ectopic pregnancy.

Ninth, the ectopic pregnancy treatment catheter and the catheter guide according to present invention enables more extensive selection of ectopic pregnancy treatment methods depending on the state and environmental conditions of a patient by virtue of the first catheter guide with a curved structure having a preset radius of curvature and the second catheter guide with a ductile structure movable along the first catheter guide.

Tenth, the ectopic pregnancy treatment catheter and the catheter guide according to the present invention allows a surface-processed part to be formed on the outer peripheral surface of the first catheter guide, thereby minimizing movement resistance caused by the surface tension due to liquid during the relative movement between the first and second catheter guides, and achieving prompt and smooth treatment procedures.

Eleventh, the ectopic pregnancy treatment catheter, the catheter guide, and the ectopic pregnancy treatment method using the same according to the present invention enable prompt and smooth removal of the gestational sac through a proper step depending on the state and therapeutic environment of a patient, thereby providing a more efficient ectopic pregnancy treatment method.

BRIEF DESCRIPTION OF THE DRAWINGS

The above and other objects, features and advantages of the present invention will be apparent from the following detailed description of the preferred embodiments of the invention in conjunction with the accompanying drawings, in which.

MODE FOR CARRYING OUT THE INVENTION

Now, preferred embodiments of a catheter for treating ectopic pregnancy and a catheter unit for treating ectopic pregnancy, which includes the catheter unit according to the present invention will be described hereinafter in detail with reference to the accompanying drawings. The configuration and operation of the present invention is described in one embodiment with reference to the drawings, and this embodiment does not limit the technical spirit, the core configuration, and the operation of the present invention.

In addition, as the specific terminology used in the present invention, currently widely used general terms are preferably selected. In a specific case, the present invention is described using the terms selected randomly by the applicant. In such a case, their meanings are described in the detailed description of the corresponding part. Therefore, the present invention should not be interpreted simply based on only the name of the terminology used in the description of the present invention, but should be interpreted by identifying the meaning of the corresponding terms.

Figure 1:
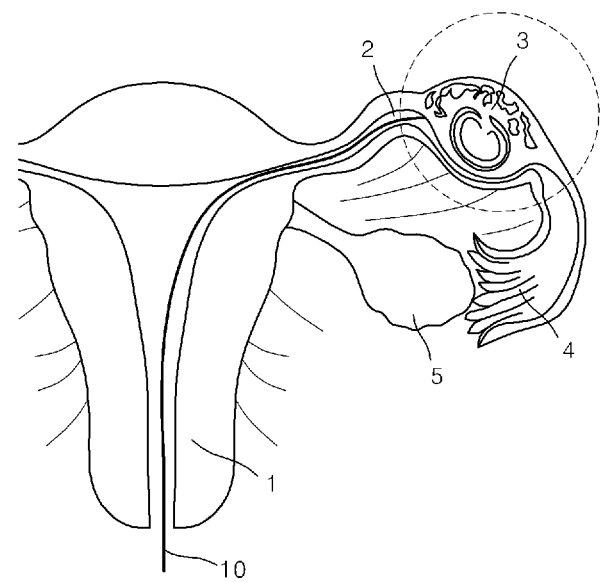
FIG. 1 is a schematic view illustrating a state in which a catheter for treating ectopic pregnancy according to an embodiment of the present invention has been inserted in vivo.
Figure 2:
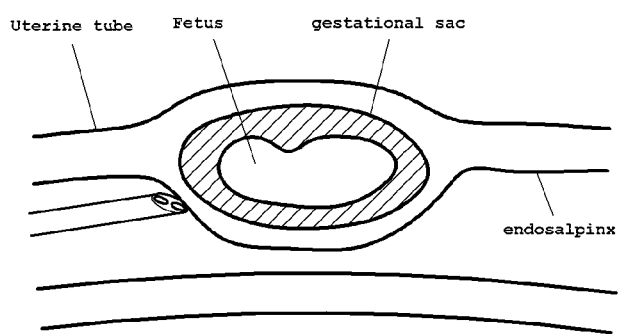
FIG. 2 is a schematic view illustrating a state in which a catheter for treating ectopic pregnancy according to an embodiment of the present invention is positioned in proximity of a gestational sac.

In the present invention, ectopic pregnancy may occur abnormally at a position other than a fallopian tube, but in the present specification, description is given of the case where ectopic pregnancy occurs in the fallopian tube 2 as shown in FIGS. 1 and 2 for the sake of facilitation of explanation.

FIG. 1 is a schematic view illustrating a state in which a catheter for treating ectopic pregnancy according to an embodiment of the present invention has been inserted in vivo.

Generally, an ovum or egg separated from an ovary 5 is fertilized with a sperm at a tubal ampulla of a fallopian tube 4, and the fertilized egg is stably transported into the uterus where implantation occurs stably. However, as shown in FIG. 1, if a gestational sac 3 is abnormally implanted at the fallopian tube 2, the fallopian tube may be ruptured due to the rapid growth of the embryo in the gestational sac 3. Therefore, the present invention is aimed at providing an ectopic pregnancy treatment catheter, which can inject a drug into the gestational sac 3 in a safer and more efficient manner to prevent the growth of the gestational sac 3.

Referring to FIG. 1, a catheter 10 for treating ectopic pregnancy according to the present invention is inserted into a vagina and then inserted into the fallopian tube 2 through a uterine cavity of an uterus 1. In addition, the ectopic pregnancy treatment catheter 10 penetrates into the gestational sac 3 and injects a pregnancy tissue-destroying drug into the gestational sac 3 so that ectopic pregnancy can be treated. Alternatively, ectopic pregnancy may be treated only with a small dose of drug by suctioning an amniotic fluid in the gestational sac 3 before injecting the pregnancy tissue-destroying drug into the gestational sac 3.

FIG. 2 is a schematic view illustrating a state in which a catheter for treating ectopic pregnancy according to an embodiment of the present invention is positioned in proximity of a gestational sac;

Referring to FIG. 2, an ectopic pregnancy treatment catheter 10 according to the present invention reaches a position where it can accurately penetrate into the gestational sac 3, and then it suctions the amniotic fluid in the gestational sac 3 and injects the drug into the gestational sac 3 so that the growth of the gestational sac 3 can be prevented.

Therefore, the ectopic pregnancy treatment catheter 10 according to the present invention should have a structure which can reach a position where it can accurately penetrate into the gestational sac 3. In addition, the ectopic pregnancy treatment catheter 10 should have a structure which can suction the amniotic fluid in the gestational sac 3 and inject the drug into the gestational sac 3.

Hereinafter, various embodiments of the ectopic pregnancy-treating catheter to which the present invention is applied will be described.

Figure 3:
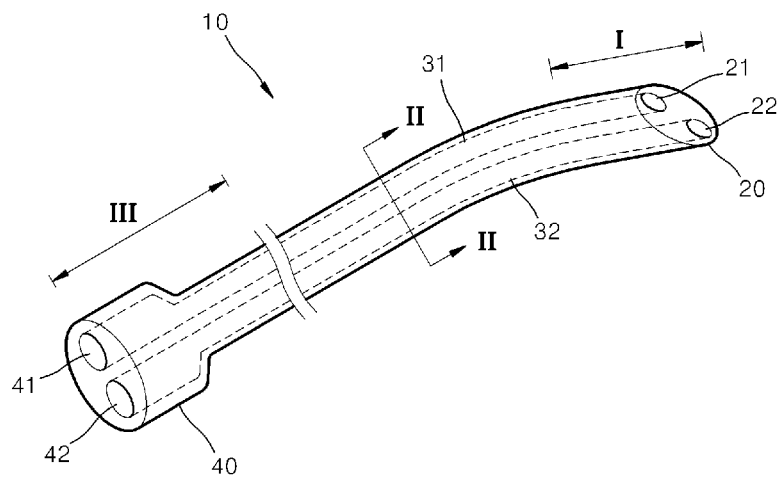
FIG. 3 is a schematic perspective view illustrating a catheter for treating ectopic pregnancy according to an embodiment of the present invention.
Figure 4:
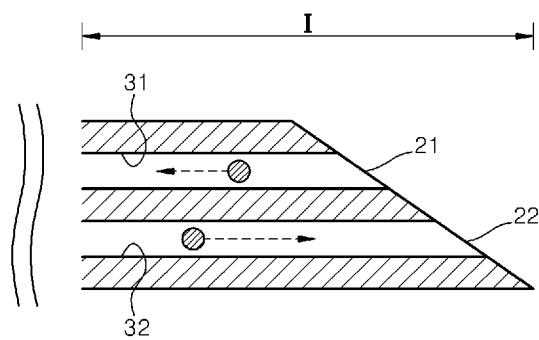
FIG. 4 is a schematic cross-sectional view illustrating a penetrating part (i.e., section I of FIG. 3) of a catheter for treating ectopic pregnancy according to an embodiment of the present invention.
Figure 5:
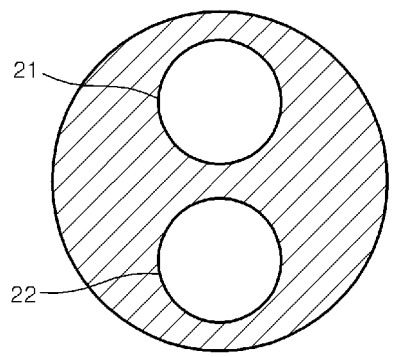
FIG. 5 is a schematic cross-sectional view taken along the line II-II of FIG. 3.
Figure 6:
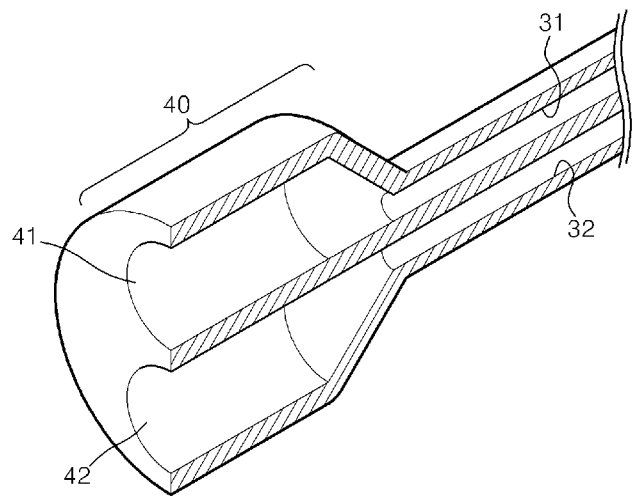
FIG. 6 is an enlarged perspective cross-sectional view illustrating a connecting part (i.e., section III of FIG. 3) of a catheter for treating ectopic pregnancy according to an embodiment of the present invention.

FIG. 3 is a schematic perspective view illustrating a catheter for treating ectopic pregnancy according to an embodiment of the present invention, and FIGS. 4 to 6 are cross-sectional and perspective cross-sectional views of each element of the catheter for treating ectopic pregnancy according to an embodiment of the present invention.

Referring to FIG. 3, the ectopic pregnancy treatment catheter 10 according to the present invention includes a penetrating part 20, a first flow passage part 31, a second flow passage part 32, and a connecting part 40.

The penetrating part 20 may be formed as a structure in which it is disposed at a front end of the ectopic pregnancy treatment catheter 10 and can be inserted in vivo through a uterine cervix. In addition, the penetrating part 20 may be formed to include a front tip end which can directly penetrate into the gestational sac. For example, the penetrating part 20 may be formed to have an inclined face in one direction as shown in FIGS. 3 and 4. FIG. 4 enlargedly shows the section of the penetrating part 20. Alternatively, the penetrating part 20 may be formed to include a front tip end at the center of the section thereof such as a conical shape (see FIG. 12 or 17). Likewise, the distal end of penetrating part 20 is formed in a pointed sharp shape so that the ectopic pregnancy treatment catheter 10 can directly penetrate into the gestational sac. In addition, since the penetrating part 20 has a relatively fine size as compared to that of the gestational sac and a predetermined stiffness (or rigidity), it can easily penetrate into the gestational sac only by applying a given pressure.

The penetrating part 20 may have at least one opening portion formed on the inclined face thereof. For example, in FIGS. 3 and 4, the penetrating part 20 may have two opening portions 21 and 22. Referring to FIG. 4, a first opening portion 21 fluidically communicates with the first flow passage part 31 so that a liquid in the gestational sac is introduced into the first flow passage part 31 through the first opening portion 21. A second opening portion 22 fluidically communicates with the second flow passage part 32 so that a liquid introduced into the second flow passage part 32 from the outside is delivered into the gestational sac through the second opening portion 22. Herein, the liquid in the gestational sac may be an amniotic fluid, and the liquid introduced into the second flow passage part 32 from the outside may be a gestational sac-eliminating drug.

FIG. 6 shows an enlarged perspective cross-sectional view of the connecting part 40.

As shown in FIG. 6, the connecting part 40 may be formed as a structure in which it is disposed at a rear end of the ectopic pregnancy treatment catheter 10 and discharges a liquid in a female body to the outside or introduces a liquid from the outside. The connecting part 40 may have at least one opening portion. For example, as shown in FIGS. 3 and 6, the connecting part 40 may include a third opening portion 41 and a fourth opening portion 42. The third opening portion 41 corresponds to the first opening portion 21 of the penetrating part 20, and the fourth opening portion 42 corresponds to the second opening portion 22 of the penetrating part 20. The third opening portion 41 fluidically communicates with the first flow passage part 31 so that the amniotic fluid of the gestational sac introduced into the first flow passage part 31 through the first opening portion 21 is discharged to the outside. In addition, the fourth opening portion 42 fluidically communicates with the second flow passage part so that a gestational sac-eliminating drug introduced into the second flow passage part 32 from the outside through the fourth opening portion 42 is delivered into the gestational sac through the second opening portion 22.

The first flow passage part 31 and the second flow passage part 32 constitutes a flow passage of the liquid introduced into the first flow passage part 31 and the second flow passage part 32 through the penetrating part 20 or the connecting part 40. The first flow passage part 31 and the second flow passage part 32 may have a proper shape to allow the introduced liquid to smoothly flow. FIG. 5 shows an enlarged cross-sectional view of the catheter for treating ectopic pregnancy including the first flow passage part 31 and the second flow passage part 32. For example, as shown in FIGS. 3 and 5, the first flow passage part 31 and the second flow passage part 32 may have an elongated cylindrical shape but the present invention is not limited thereto.

In addition, the first flow passage part 31 may be formed to have a diameter enough for the catheter to suction the liquid in the gestational sac, and the second flow passage part 32 may be formed to have a diameter enough for the catheter to inject the liquid introduced from the outside into the gestational sac. For example, referring to FIGS. 3 and 6, the diameter of the third opening portion 41 (or the fourth opening portion 42 of the connecting part 40 may be different from that of the first opening portion 21 (or the second opening portion 22) of the penetrating part 20. When the ectopic pregnancy treatment catheter 10 is inserted in vivo, the connecting part 40 should be connected to a suction device or an injection device at the outside of the body. A syringe may be taken as an example of the suction device or the injection device. In this case, the third opening portion (or the fourth opening portion 42) of the connecting part 40 will have to a diameter enough to be capable of being coupled to a connecting portion of the suction device or the injection device. Thus, the diameter of the third opening portion 41 (or the fourth opening portion 42) of the connecting part 40 may be larger than that of the first opening portion 21 (or the second opening portion 22) of the penetrating part 20.

In this embodiment, the connecting part 40 is formed integrally with the ectopic pregnancy treatment catheter 10, but the present invention is not limited thereto. For example, the connecting part 40 may be provided as a structure which is formed as a separate member that can be coupled to the ectopic pregnancy treatment catheter 10.

In another embodiment, the first flow passage part 31 (or the second flow passage part 32) may have the same diameter in its entirety along a lengthwise direction thereof. Alternatively, the first flow passage part 31 (or the second flow passage part 32) may have a diameter which is gradually decreased or increased in the direction of the flow of liquid. In this case, the first flow passage part 31 serves as a path along which the liquid in the gestational sac is suctioned so that the liquid flows toward the third opening portion 41 from the first opening portion 21. The second flow passage part 32 serves as a path along which the gestational sac-eliminating drug is injected into the gestational sac so that the drug flows toward the second opening portion 22 from the fourth opening portion 42.

Likewise, when the ectopic pregnancy treatment catheter 10 is inserted in vivo to cause the penetrating part 20 to penetrate into the gestational sac, the third opening portion 41 of the connecting part 40 is connected to the suction device to suction the amniotic fluid in the gestational sac, and the fourth opening portion 42 of the connecting part 40 is connected to the injection device to inject a drug such as methotrexate into the gestational sac. Likewise, the amniotic fluid in the gestational sac is discharged to the outside of the body through the first flow passage part 31 so that when the drug is injected into the gestational sac, it can be activated effectively. In addition, the drug is directly injected into the gestational sac through the second flow passage part 32 so that ectopic pregnancy can be treated only with a small dose of the drug without any surgical procedures.

The ectopic pregnancy treatment catheter 10 according to the present invention may have the following characteristics so that when the catheter is inserted in vivo, it can reach the gestational sac safely. For example, the ectopic pregnancy treatment catheter 10 may have a predetermined stiffness or rigidity to control the progress direction thereof so that it reaches the gestational sac safely after being inserted in vivo, or may have a predetermined ductility to prevent the body from being damaged due to any contact in vivo. Alternatively, the ectopic pregnancy treatment catheter 10 may have a structure in which it is curved or bent to fit the bodily structure formed by of the vaginal cavity, the uterine cervix, and the fallopian tube of a female patient. In addition, the ectopic pregnancy treatment catheter 10 may have a length enough to be capable of reaching the gestational sac through vaginal cavity, the uterine cervix, and the fallopian tube. In addition, the ectopic pregnancy treatment catheter 10 may be formed of a material harmful to the human body. Examples of the material for the catheter 10 include silicon, polyethylene, latex, polytetrafluoroethylene (PTFE), polyurethane, polyether block amid copolymer, polyether polyamid polyester multiblock copolymer.

In another embodiment, the penetrating part 20 may formed integrally with the ectopic pregnancy treatment catheter 10, but may be formed as a separate structure. For example, the penetrating part 20 may be formed as a structure in which it can be detachably mounted to the distal end of the ectopic pregnancy treatment catheter 10.

Figure 7:
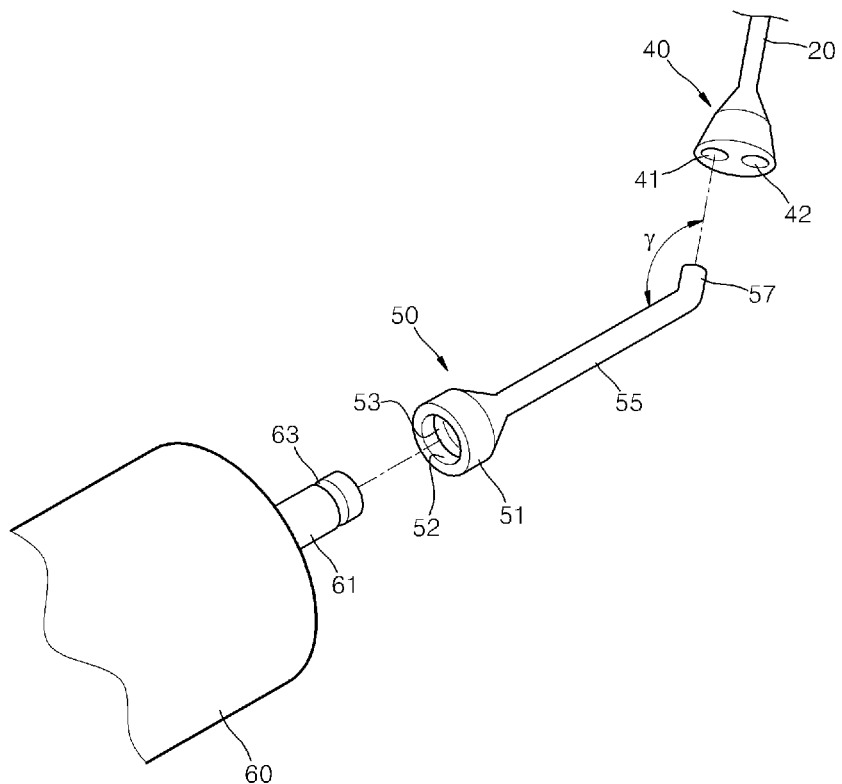
FIG. 7 is a partially enlarged perspective view illustrating a connecting part of a catheter for treating ectopic pregnancy, a catheter connector, and one end of a syringe, which are disassembled from each other, according to an embodiment of the present invention.
Figure 8:
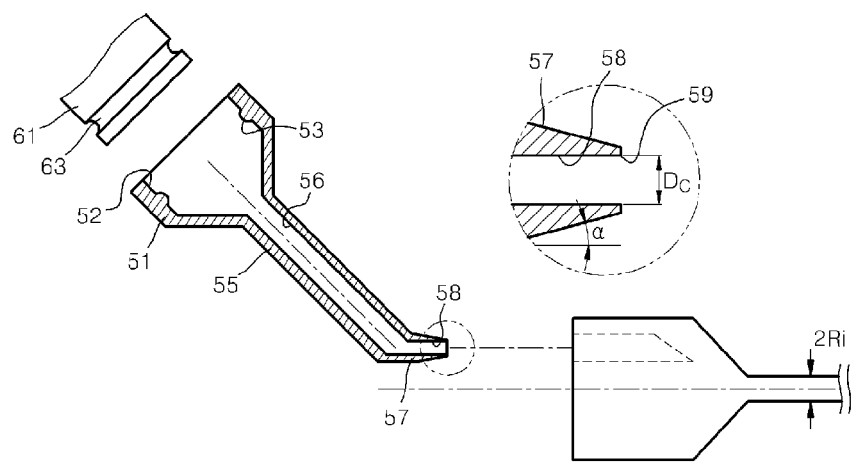
FIG. 8 is a schematic partially enlarged cross-sectional view illustrating a connecting part of a catheter for treating ectopic pregnancy, a catheter connector, and one end of a syringe, which are disassembled from each other, according to an embodiment of the present invention.

FIGS. 7 and 8 partially enlarged perspective views illustrating a distal end of an ectopic pregnancy treatment catheter, a catheter connector, and a suction device (or an injection device), which are disassembled from each other, according to an embodiment of the present invention;

The ectopic pregnancy treatment catheter 10 according to the present invention may be directly connected to a suction device (or an injection device), but may be connected to the suction device (or the injection device) by means of a separate catheter connector in another embodiment as shown in FIG. 7.

As shown in FIGS. 7 and 8, the catheter connector 50 applied to the present invention may include a connector body 51, a connector coupler 52, a connector line portion 55, and a connector line extending portion 57.

The catheter connector 50 may include the connector line portion 55 extending from the connector body 51 and the connector line extending portion 57 extending from an end of the connector line portion 55. One end of the catheter connector 50 is detachably connected to the third opening portion 41 (or the fourth opening portion 42) of the connecting part 40 so as to fluidically communicate with the first flow passage part 31 (or the second flow passage part 32). In addition, at the other end of the catheter connector 50 is provided the connector coupler 52 which can be connected to the suction device (or the injection device). In this case, the connector coupler 52 may have a diameter enough to be capable of being connected to the injection device (or the suction device), for example, a syringe inlet 61 shown in FIGS. 7 and 8.

The connector body 51 and the connector line portion 55 are positioned on a coaxial line, and the catheter connector 50 may take a structure in which the central line of the connector line extending portion 57 forms an connector angle (γ) indicated by a reference symbol γ together with an axial line formed by the connector body 51 and the connector line portion 55. Likewise, the connector angle (γ) is formed as an obtuse angle so that interference is prevented from occurring between other catheter connectors connected to the connecting part 40 of the ectopic pregnancy treatment catheter or between the suction device and the injection device connected to the catheter connectors.

In addition, referring to FIG. 8, the outer periphery of the connector line extending portion 57 may be tapered to have an inclined face formed at an angle α. This is merely illustrative of the present invention to facilitate the engagement between the connector line extending portion 57 and the third opening portion 41 (or the fourth opening portion 42) of the connecting part 40, but the present invention is not limited thereto. The connector line extending portion 57 has a connecting line extending through-hole 58 formed therein and the connector line portion 55 has a connecting line through-hole 56 formed therein. In this case, the connecting line through-hole 56 interconnects the connecting line extending through-hole 58 having a diameter Dco and the connector coupler 52. Further, the connecting line through-hole 56, the connecting line extending through-hole 58, and the connector coupler 52 may take a structure in which there occurs a gradual change in cross-section to smoothly cope with the pressure change caused by a difference in diameter In another embodiment of the present invention, the catheter connector 50 may further include an element for ensuring the connection with the injection device (or the suction device) such as a syringe. For example, as shown in FIGS. 7 and 8, the connector coupler 52 may have a connector engagement portion 53 formed on the inner peripheral surface thereof. The connector engagement portion 53 may take a salient structure which is protruded inwardly from the inner peripheral surface of the connector coupler 52. A counterpart connector engagement portion 63 having a shape corresponding to that of the connector engagement portion 53 may be formed on the outer peripheral surface of the syringe inlet 61. Likewise, the connector coupler 52 and the syringe inlet 61 are engaged with each other in a press-fit engagement manner so that the inside of an assembly of the connector coupler 52 and the syringe inlet 61 can be maintained in a tightly sealed state, and the syringe 60 can be prevented from being undesirably separated from the catheter connector 50.

This is merely illustrative of the present invention, and the present invention is not limited thereto. For example, the connector engagement portion 53 may be formed as a grooved structure, and the counterpart connector engagement portion 63 may be formed as a salient structure. Alternatively, the connector coupler 52 may have a tapered structure formed on the inner peripheral surface thereof to take a press-fit engagement structure.

Figure 9:
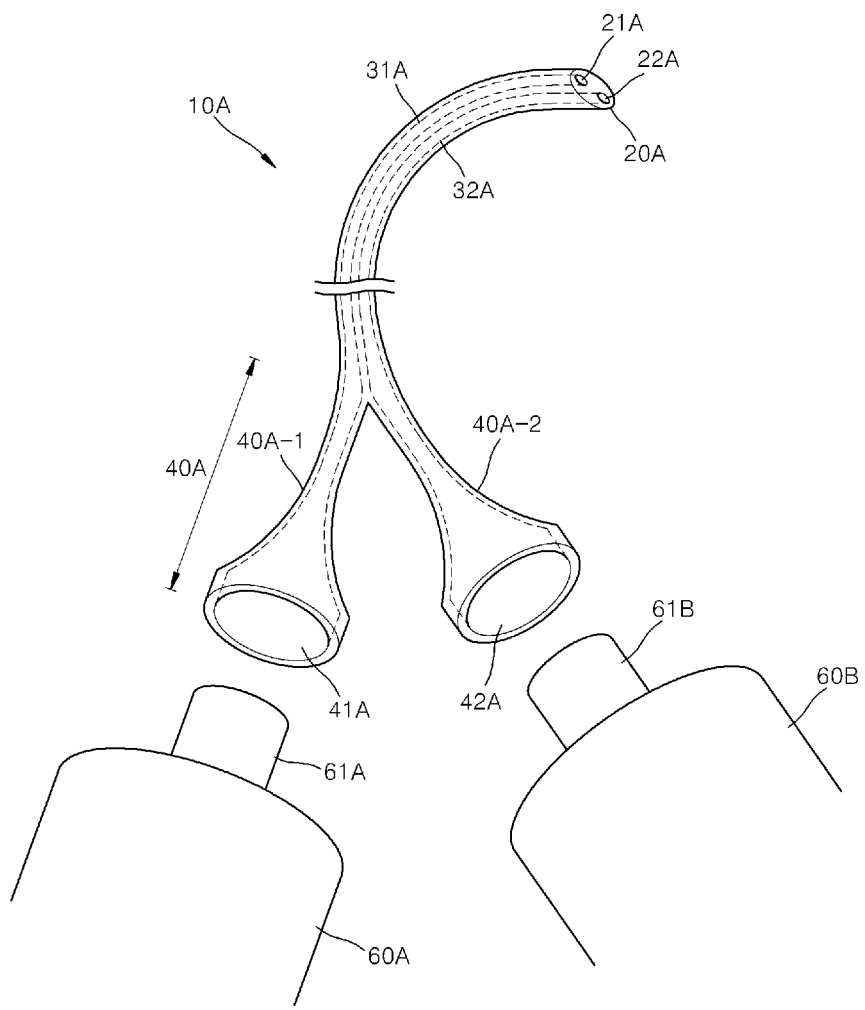
FIG. 9 is a schematic perspective view illustrating a catheter for treating ectopic pregnancy according to another embodiment of the present invention.

FIG. 9 is a schematic perspective view illustrating a catheter for treating ectopic pregnancy according to another embodiment of the present invention.

Referring to FIG. 9, the catheter 10A for treating ectopic pregnancy according to another embodiment of the present invention may include a penetrating part 20A, a first flow passage part 31A, a second flow passage part 32A, and a connecting part 40A. The penetrating part 20A may include a first opening portion 21A and a second opening portion 22A, and the connecting part 40A may include a first connecting part 40A-1 and a second connecting part 40A-2.

The penetrating part 20A may be formed as a structure in which it is disposed at a front end of the catheter 10A for treating ectopic pregnancy and can be inserted into a female body through a uterine cervix. In regard to the characteristics of the penetrating part 20A, various characteristics described with reference to FIGS. 3 and 4 are all applied to this embodiment, and thus the detailed description thereof will be omitted to avoid redundancy.

The connecting part 40A may be formed as a structure in which it is branched off into the first connecting part 40A-1 and the second connecting part 40A-2 so as to be coupled to external syringe tools. For example, the first connecting part 40A-1 is connected to a drug injection tool 60A so that a pregnancy tissue-destroying drug is introduced into the first connecting part 40A-1 from the drug injection tool 60A. Then, the drug introduced into the first connecting part 40A-1 is delivered into the gestational sac through the first opening portion 21A. In addition, the second connecting part 40A-2 is connected to an amniotic fluid suction tool 60B so that an amniotic fluid from the gestational sac is suctioned by the amniotic fluid suction tool 60B through the second opening portion 22A. The amniotic fluid suctioned by the amniotic fluid suction tool 60B is transferred to the amniotic fluid suction tool 60B.

In this case, the first connecting part 40A-1 may include a third opening portion 41A and the second connecting part 40A-2 may include a fourth opening portion 42A. The third opening portion 41A is connected to the first flow passage part 31A and the first opening portion 21A to form a through-hole such that the diameter of the third opening portion 41A is larger than that of the first opening portion 21A. For example, the diameter of the third opening portion 41A corresponds to that of an injection portion 61A of the drug injection tool 60A. In addition, the fourth opening portion 42A is connected to the second flow passage part 32A and the second opening portion 22A to form a through-hole such that the diameter of the fourth opening portion 42A is larger than that of the second opening portion 22A. For example, the diameter of the fourth opening portion 42A corresponds to that of a suction portion 61B of the amniotic fluid suction tool 60B.

Moreover, it has been shown in FIG. 9 that the third opening portion 41A and the injection portion 61A of the drug injection tool 60A are engaged with each other in a simple fit engagement manner, but the present invention is not limited thereto. For example, as shown FIGS. 7 and 8, the third opening portion 41A and the injection portion 61A of the drug injection tool 60A may be engaged with each other in a press-fit engagement manner so that the inside of an assembly of the third opening portion 41A and the injection portion 61A can be maintained in a tightly sealed state. In addition, the drug injection tool 60A or the amniotic fluid suction tool 60B are prevented from undesirably being separated from the catheter 10A for treating ectopic pregnancy due to a pressure generated by injection or suction of the drug injection tool 60A or the amniotic fluid suction tool 60B. This is merely illustrative of the present invention, and the present invention is not limited thereto. For example, the third opening portion 41A and the injection portion 61A of the drug injection tool 60A may be engaged with each other in a screw engagement manner so that the drug injection tool 60A or the amniotic fluid suction tool 60B can be prevented from being separated from the catheter 10A.

Similarly, In regard to the characteristics of each element of the catheter 10A for treating ectopic pregnancy according to the present invention, various characteristics described in other embodiments are all applied to this embodiment, and thus the detailed description thereof will be omitted to avoid redundancy.

Figure 10:
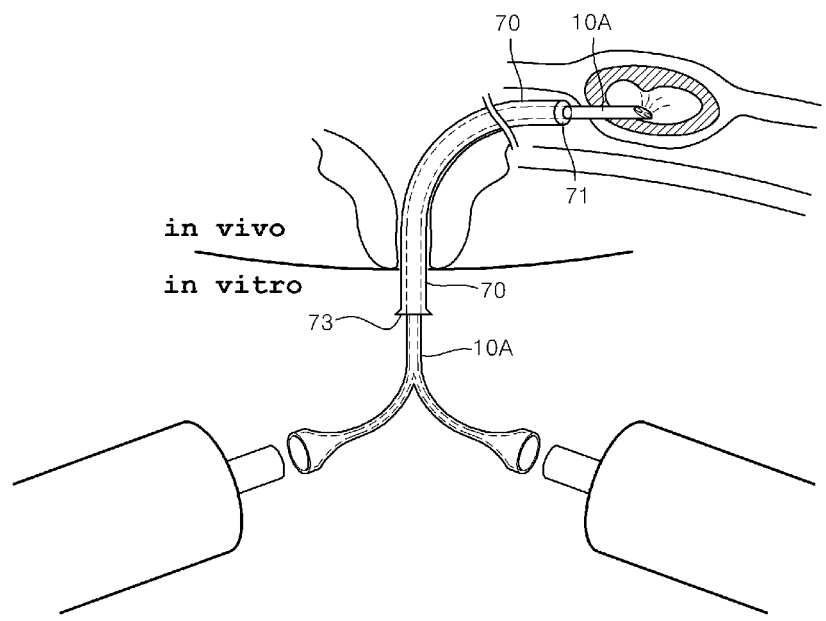
FIG. 10 is a schematic view illustrating a state in which a catheter for treating ectopic pregnancy of FIG. 9, according to another embodiment of the present invention has been inserted in vivo.

FIG. 10 is a schematic view illustrating a state in which a catheter for treating ectopic pregnancy of FIG. 9, according to another embodiment of the present invention has been inserted in vivo;

Referring to FIG. 10, first, a catheter guide 70, which will be described later, is inserted into the fallopian tube and is positioned at a front end thereof in front of the gestational sac. In addition, the catheter 10A for treating ectopic pregnancy according to the present invention is inserted into the catheter 70 through a rear distal end 73 of the catheter guide 70, and the catheter 10A for treating ectopic pregnancy can safely reach the gestational sac along a guide through-part 72 in a state in which a path for entry into the fallopian tube has been previously secured.

As shown in FIG. 10, the front end of the catheter 10A for treating ectopic pregnancy penetrates into the gestational sac after perforating through a membrane of the front end part 71. The amniotic fluid in the gestational sac is suctioned using the amniotic fluid suction tool 60B, and then a pregnancy tissue-destroying drug is injected into the gestational sac using the drug injection tool 60A. Through this process, ectopic pregnancy can be treated in a safer and more accurate manner.

The catheter guide 70 according to the present invention may have the following characteristics so that when the catheter guide 70 is inserted in vivo, it can reach the gestational sac safely. For example, the catheter guide 70 may have a predetermined stiffness or rigidity to control the progress direction thereof so that it reaches the gestational sac safely after being inserted in vivo, or may have a predetermined ductility to prevent the body from being damaged due to any contact in vivo. Alternatively, the catheter guide 70 may have a structure in which it is curved or bent to fit the bodily structure formed by of the vaginal cavity, the uterine cervix, and the fallopian tube of a female patient. In addition, the catheter 10A for treating ectopic pregnancy and the catheter guide 70 may have a length enough to be capable of reaching the gestational sac through vaginal cavity, the uterine cervix, and the fallopian tube. In addition, the catheter 10A for treating ectopic pregnancy and the catheter guide 70 may be formed of a material harmful to the human body. Examples of the material for the catheter 10A and the catheter guide 70 include silicon, polyethylene, latex, polytetrafluoroethylene (PTFE), polyurethane, polyether block amid copolymer, polyether polyamid polyester multiblock copolymer.

Figure 11:
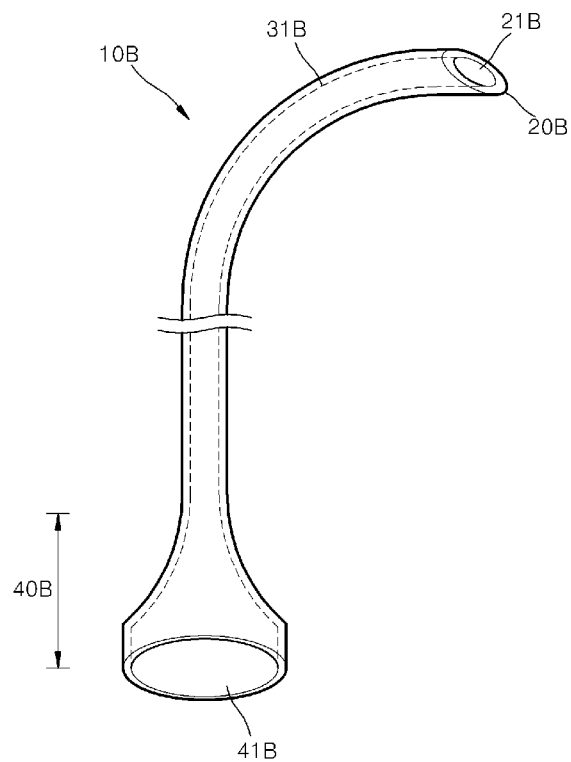
FIG. 11 is a schematic perspective view illustrating a catheter for treating ectopic pregnancy according to another embodiment of the present invention.

FIG. 11 is a schematic perspective view illustrating a catheter for treating ectopic pregnancy according to another embodiment of the present invention.

Referring to FIG. 11, a catheter 10B for treating ectopic pregnancy according to the present invention may include a penetrating part 20B, a flow passage part 31B, and a connecting part 40B. The penetrating part 20B may include a first opening portion 21B, and the connecting part 40B may include a second opening portion 41B.

This embodiment provides the catheter 10B for treating ectopic pregnancy, which performs the combined function of amniotic fluid suction and drug injection through a single flow passage part 31B. For example, first, the amniotic fluid suction tool is connected to the catheter 10B through the connecting part 40B to suction the amniotic fluid in the gestational sac. Thereafter, the amniotic fluid suction tool is separated from the catheter 10B and then the drug injection tool is connected to the catheter 10B to inject the drug into the gestational sac so that ectopic pregnancy can be treated.

In addition, this embodiment provides the catheter 10B for treating ectopic pregnancy through only a drug injection process. For example, the amniotic fluid suction process is excluded, and the drug injection tool is connected to the catheter 10B to inject the drug into the gestational sac so that ectopic pregnancy can be treated.

Figure 12:
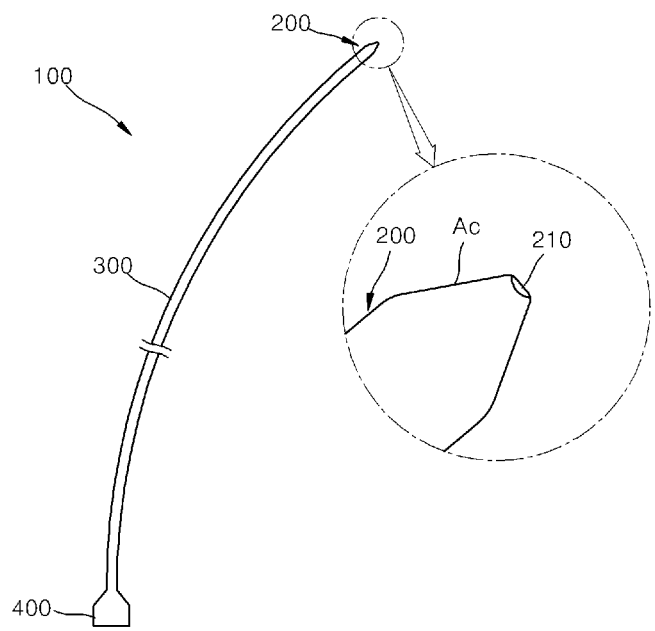
FIG. 12 is a schematic perspective and partially enlarged view illustrating a catheter for treating ectopic pregnancy according to another embodiment of the present invention.
Figure 13:
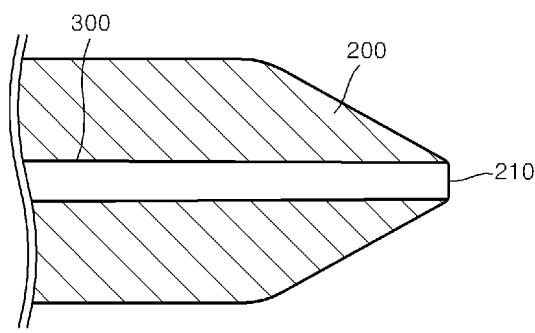
FIG. 13 is a schematic cross-sectional view illustrating a penetrating part of a catheter for treating ectopic pregnancy of FIG. 12, according to another embodiment of the present invention.

FIGS. 12 and 13 are schematic perspective and partially enlarged views illustrating a catheter for treating ectopic pregnancy, including a single flow passage part according to another embodiment of the present invention is positioned in proximity of a gestational sac.

The catheter 100 for treating ectopic pregnancy according to the present invention may include at least one flow passage part. In FIG. 12, there is shown an ectopic pregnancy treatment catheter, which includes a single flow passage part.

The catheter 100 for treating ectopic pregnancy includes a penetrating part 200, a flow passage part 300, and a connecting part 400.

The penetrating part 200, the flow passage part 300, and the connecting part 400 may adopt all the characteristics described in the above embodiments of FIGS. 1 to 8, and a difference between the above embodiments and this embodiment and its characteristics only will be described in this embodiment.

Referring to FIG. 12, the penetrating part 200 may be implemented in a tapered shape which is gradually reduced in diameter as it goes toward a front end thereof like a conical shape in which an inclined face Ac is formed at a front end of the penetrating part 200.

The penetrating part 200 may have at least one opening portion formed at a front tip end thereof. For example, in FIG. 13, the penetrating part 200 may have a single fifth opening portion 210. As shown in FIG. 12, the fifth opening portion 210 fluidically communicates with the flow passage part 300 so that a liquid in the gestational sac is introduced into the flow passage part 300 through the fifth opening portion 210 or a liquid introduced into the flow passage part 300 from the outside is delivered into the gestational sac through the fifth opening portion 210. Herein, the liquid in the gestational sac may be an amniotic fluid and the liquid introduced into the flow passage part 300 from the outside may be a gestational sac-eliminating drug.

The connecting part 400 may be formed as a structure in which it is disposed at a rear end of the catheter 100 for treating ectopic pregnancy and discharges a liquid in a female body to the outside or introduces a liquid from the outside. The connecting part 400 may have a sixth opening portion (not shown). The sixth opening portion (not shown) corresponds to the fifth opening portion 210 of the penetrating part 200. The sixth opening portion (not shown) fluidically communicates with the flow passage part 300 so that the amniotic fluid in the gestational sac introduced into the flow passage part 300 through the fifth opening portion 210 is discharged to the outside through the sixth opening portion (not shown) or the gestational sac-eliminating drug introduced into the flow passage part 300 from the outside through the sixth opening portion (not shown) is injected into the gestational sac through the fifth opening portion 210. The amniotic fluid discharge process and the drug injection process may be performed selectively. For example, the amniotic fluid discharge process is excluded if necessary, and ectopic pregnancy may be treated by only the drug injection process.

FIGS. 14 to 21 show various modifications of a catheter for treating ectopic pregnancy according to different embodiments of the present invention.

Figure 14:
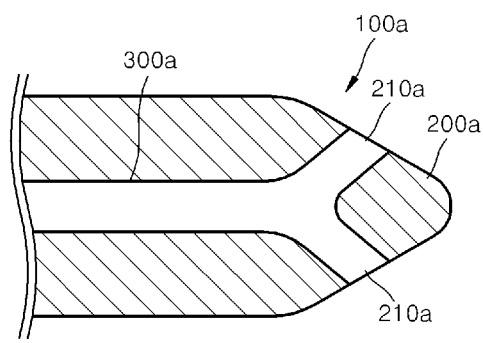
FIG. 14 is a schematic enlarged cross-sectional view illustrating a modification of a penetrating part of a catheter for treating ectopic pregnancy of according to another embodiment of the present invention.
Figure 15:
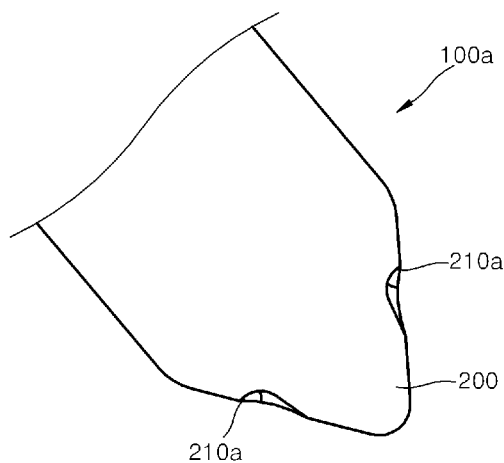
FIG. 15 is a schematic perspective view illustrating a catheter for treating ectopic pregnancy of FIG. 14, according to another embodiment of the present invention.

FIG. 14 shows a partial cross-sectional view of a catheter for treating ectopic pregnancy, which includes a flow passage part and a penetrating part having two opening portions, and FIG. 15 shows a perspective view of FIG. 14.

In FIGS. 12 and 13, when the ectopic pregnancy treatment catheter enters the body, there is a possibility that an in vivo liquid or secretion will be introduced into the flow passage part 300 through the fifth opening portion 210. Thus, when the amniotic fluid in the gestational sac is suctioned or the gestational sac-eliminating drug is injected into the gestational sac, there may occur a problem of reducing the therapeutic effect. In addition, the fifth opening portion 210 is positioned at the center of the penetrating part 200, and thus the therapeutic effect may be disadvantageously reduced during paracentesis of the gestational sac.

Therefore, an ectopic pregnancy treatment catheter according to another embodiment according to the present invention including a single flow passage part, which can solve the above-mentioned problems, will be described hereinafter.

It has been shown in FIG. 13 that the opening portion 210 of the penetrating part 200 fluidically communicating with the flow passage part 300 is formed only in single number at the front tip end of the catheter 100, but the present invention is not limited thereto. In other words, as shown in FIGS. 14 and 15, the opening portion 210a of the catheter 100a for treating ectopic pregnancy may be formed on the outer peripheral surface of the inclined face of the penetrating part 200a, but not at the center of the penetrating part 200a. In addition, the opening portion 210a may be provided in plural numbers.

Referring to FIG. 14, the flow passage part 300a may be internally formed along a lengthwise direction of a body of the catheter 100a for treating ectopic pregnancy, and may be branched off into two flow passage parts within the penetrating part 200a so as to fluidically communicate with a plurality of opening portions 210a. By virtue of this structure, paracentesis of gestational sac, endosalpinx and the like can be smoothly performed using the front tip end of the penetrating part 200a. Besides, the opening portions 210a have a structure in which they are formed on the inclined face of the penetrating part 200a, so that when paracentesis of the gestational sac is performed, the flow passage part 300a can be prevented from being clogged due to a ruptured tissue or an in vivo foreign substances.

Figure 16:
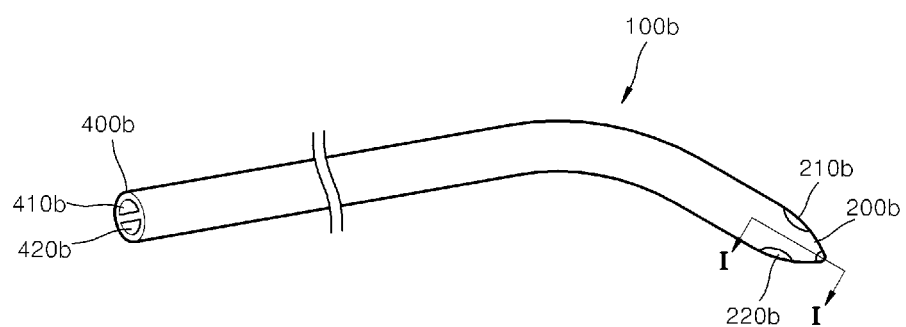
FIG. 16 is a schematic perspective view illustrating a catheter for treating ectopic pregnancy according to another embodiment of the present invention.
Figure 17:
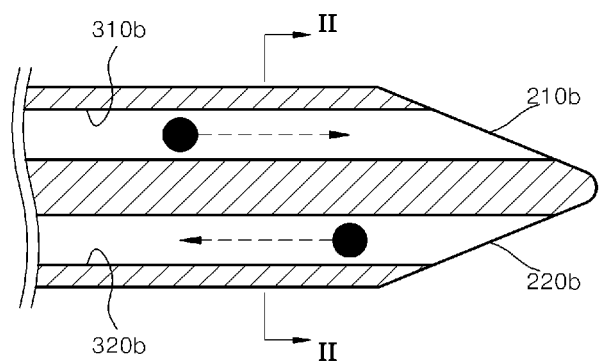
FIG. 17 is a schematic partially enlarged cross-sectional view taken along the line I-I of FIG. 16.
Figure 18:
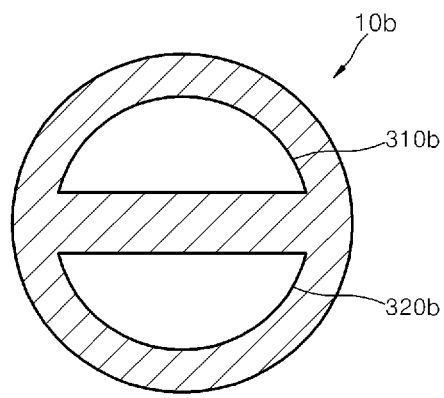
FIG. 18 is a cross-sectional view taken along the line II-II of FIG. 17.

FIG. 16 is a schematic perspective view illustrating a catheter for treating ectopic pregnancy according to another embodiment of the present invention, FIG. 17 is a schematic partially enlarged cross-sectional view taken along the line I-I of FIG. 16, and FIG. 18 is a cross-sectional view taken along the line II-II of FIG. 17.

In another embodiment of the present invention, a catheter 100b for treating ectopic pregnancy may include a plurality of flow passage parts. Similarly, in this embodiment, a difference between this embodiment and the above embodiments and its characteristics only will be described in this embodiment. Also, it is obvious to a person of ordinary skill in the art that this embodiment can directly adopt or combine the above-mentioned various characteristics.

The catheter 100b for treating ectopic pregnancy of FIGS. 16 and 18 includes a penetrating part 200b, seventh flow passage part 310b, an eighth flow passage part 320b, and a connecting part 400b. In FIG. 17, the seventh flow passage part 310b and the eighth flow passage part 320b may adopt all the characteristics of the first flow passage part 31 and the second flow passage part 32, which have been described in the above embodiments of FIGS. 3 to 6. In addition, the penetrating part 200b has a structure in which it is formed in a curved shape to minimize damage of other organs when it enters the body as shown in FIGS. 12 to 15, and the opening portions 210b and 220b have a structure in which they are formed on the inclined face of the penetrating part 200b, so that paracentesis of the gestational sac can be efficiently performed.

FIG. 18 is a schematic cross-sectional view taken along the line II-II of FIG. 17. The catheter 100b for treating ectopic pregnancy may take a stable structure in which the cross sections of the seventh flow passage part 310b and the eighth flow passage part 320b have shapes that are symmetrical with each other.

Figure 19:
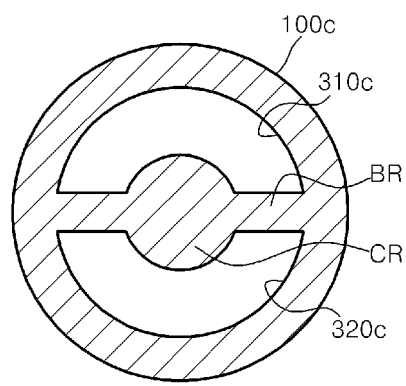
FIGS. 19 to 21 are views illustrating various examples of a section of a catheter for treating ectopic pregnancy of FIG. 14, according to another embodiment of the present invention.
Figure 20:
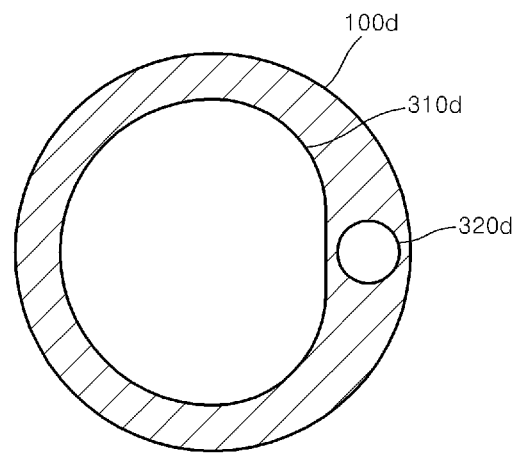
Figure 21:
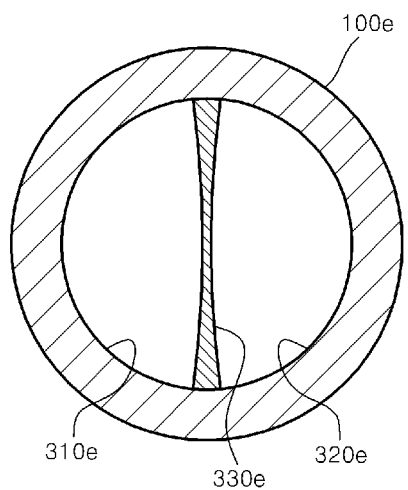

In another embodiment of the present invention, the cross-sectional shape of the flow passage parts of the catheter 100b for treating ectopic pregnancy may be configured in various manners. FIGS. 19 to 21 show various modifications of the cross section of an ectopic pregnancy treatment catheter 10 according to the present invention.

A catheter 100c for treating ectopic pregnancy shown in FIG. 19 may include a pair of flow passage parts 310c and 320c having a semicircular symmetrical shape in cross section such that it has a catheter support core CR and a catheter support bridge BR formed therein. By virtue of this configuration, deformation of the catheter 100c for treating ectopic pregnancy due to a negative pressure applied to the flow passage parts can be avoided in the amniotic fluid suction process or the drug injection process.

Meanwhile, it has been described in the above embodiment that the cross sections of the plurality of the flow passage parts have a symmetrical shape, but the present invention is not limited thereto. The flow passage parts 310d and 320d may have a non-symmetrical shape in cross section so that the flow passage parts can be prevented from being clogged and the position of the catheter 100d for treating ectopic pregnancy can be prevented from being changed as in the case of a catheter 100d for treating ectopic pregnancy shown in FIG. 20. For example, if the amount of liquid suctioned is larger than that of liquid injected, the flow passage part forming a suction flow passage may be clogged, and intermittent clogging of the flow passage part causes a change in the internal pressure of the flow passage part so that the catheter 100d for treating ectopic pregnancy can be displaced. Thus, ectopic pregnancy can be treated in a safer and more accurate manner through the non-symmetrical structure of the cross section of the flow passage part.

In another embodiment of the present invention, as shown in FIG. 21, a catheter 100e for treating ectopic pregnancy of the present invention may have a structure in which it includes flow passage parts formed as an integral piece such that a membrane 330e is centrally formed at the inside of the catheter to partition the internal space of the catheter into a flow passage part 310e for suction and a flow passage part 320e for injection. In the case where the catheter 100e for treating ectopic pregnancy is configured to perform an alternative selection of the drug injection process and the amniotic fluid suction process, the membrane 330e having a flexible structure can be shifted horizontally inside the flow passage parts, leading to a change in the internal volume of the flow passage parts 310e and 320e, so that even if the amount of liquid suctioned is relatively large, a risk of clogging of the flow passage part for suction can be avoided.

Figure 22:
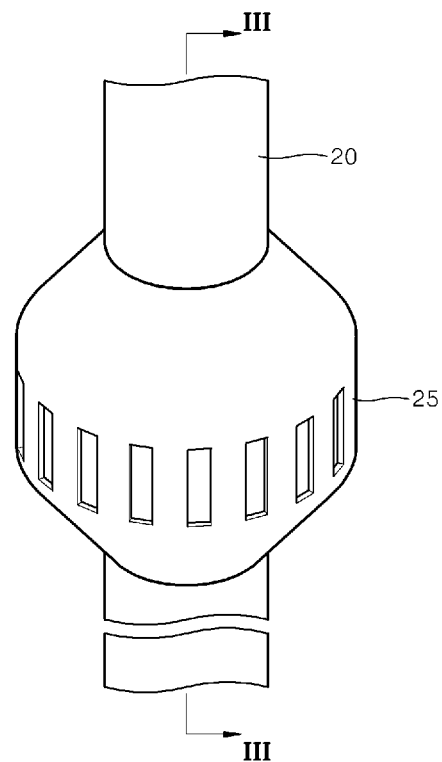
FIG. 22 is a schematic partially enlarged perspective view illustrating a direction control unit of a catheter for treating ectopic pregnancy according to another embodiment of the present invention.
Figure 23:
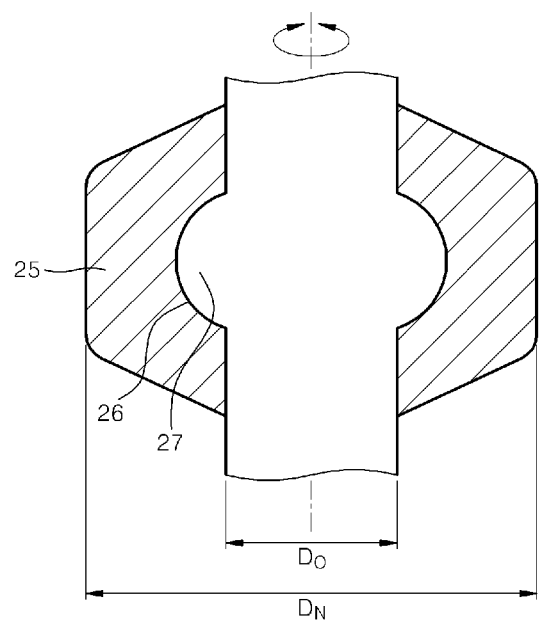
FIG. 23 is an enlarged perspective cross-sectional view taken along the line III-III of FIG. 22.

FIG. 22 is a schematic partially enlarged perspective view illustrating a direction control unit of a catheter for treating ectopic pregnancy according to another embodiment of the present invention, and FIG. 23 is an enlarged perspective cross-sectional view taken along the line III-III of FIG. 22.

The ectopic pregnancy treatment catheter 10 according to the present invention may include a control element for adjusting the progress direction of the catheter 10. For example, as shown in FIGS. 22 and 23, the ectopic pregnancy treatment catheter may further include a control knob 25. The control knob 25 may be provided on the outer peripheral surface of the ectopic pregnancy treatment catheter.

The outer diameter Dn of the control knob 25 is larger than the inner diameter of the control knob 25, so that the ectopic pregnancy treatment catheter, which is formed as a fine tube, can be adjusted finely and smoothly. In addition, the ectopic pregnancy treatment catheter may have a projection 27 formed on the outer peripheral surface thereof to prevent the relative rotation between the control knob 25 and the ectopic pregnancy treatment catheter. Thus, the control knob 25 may have a counterpart recess 26 formed on the inner peripheral surface thereof to correspond to the projection 27 so that the projection 27 is engaged with the counterpart recess 26. If the control knob 25 is injection-molded of a material such as silicon or the like, the counterpart recess 26 thereof may have a structure in which it is accompanied by the projection 27 in a solidification process of the control knob 25. FIG. 23 is merely illustrative of an embodiment of a structure for fixing the control knob 25, and the present invention is not limited thereto.

The catheters for treating ectopic pregnancy described in the above embodiments of FIGS. 1 to 23 is implemented as a fine tube structure, and thus the in vivo insertion thereof and the accurate control of the progress direction thereof after the in vivo insertion thereof may be difficult. Therefore, the present invention may employ a catheter guide to perform the treatment of ectopic pregnancy in a safer and more accurate manner using the catheters for treating ectopic pregnancy described in the above embodiments of FIGS. 1 to 23. Therefore, the present invention can provide the catheter unit for treating ectopic pregnancy, which includes the ectopic pregnancy treatment catheter and the catheter guide.

Figure 24:
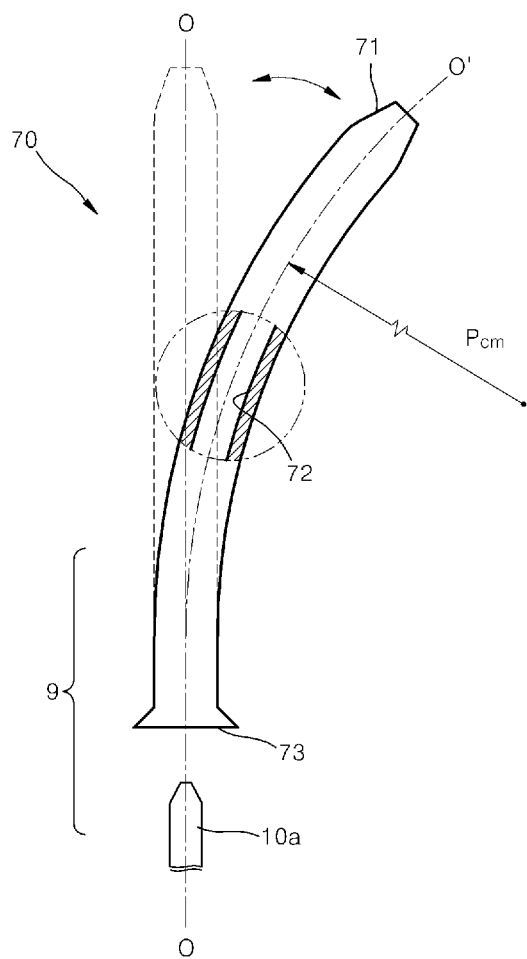
FIG. 24 is a schematic enlarged perspective view illustrating a catheter guide for guiding an entry of a catheter for treating ectopic pregnancy into the female body, according to an embodiment of the present invention.

FIG. 24 is a schematic enlarged perspective view illustrating a catheter guide for guiding an entry of a catheter for treating ectopic pregnancy into a female body, according to an embodiment of the present invention.

The catheter unit 9 for treating ectopic pregnancy according to the present invention may include the catheter 10A for treating ectopic pregnancy and the catheter guide 70. The length of the catheter guide 70 may be formed to be shorter than that of the catheter 10A for treating ectopic pregnancy, and the diameter of the catheter guide 70 may be formed to be larger than that of the catheter 10A for treating ectopic pregnancy. The reason for this is to facilitate the insertion of the catheter 10A for treating ectopic pregnancy into the catheter guide and the control of the progress direction of the catheter 10A.

Referring to FIG. 24, the catheter guide 70 may include a front end part 71, a guide through-part 72, and a rear end part 73. When the catheter guide 70 is inserted in vivo, the front end part 71 is introduced in vivo and the rear end part 73 is positioned in vitro. The guide through-part 72 is connected at one end thereof to the front end part 71 and is connected at the other end thereof to the rear end part 73. The guide through-part 72 is formed inside the catheter guide 70 to guide a path for entry of the catheter 10A for treating ectopic pregnancy into the catheter guide 70 so the catheter 10A can reach the gestational sac safely and accurately.

In addition, the catheter guide 70 is formed as a physical adaptive structure so that the catheter 10A for treating ectopic pregnancy can reach the gestational sac more safely and accurately. For example, the catheter guide 70 may be formed as a curved structure having a preset radius of curvature (ρcm). As shown in FIG. 24, the catheter guide 70 may be formed as a structure in which a central line (O-O') is curved or bent by a preset radius of curvature (ρcm) from a reference line (O-O) in the form of a straight line. The reason for this is that the fallopian tubes are positioned eccentrically to the left and right by a preset radius of curvature (ρcm) with respect to the uterus (see FIG. 1). Therefore, in the case where the catheter guide 70 is formed as a curved structure that fits a bodily structure, it can secure a more stable position in vivo. Furthermore, even in the case where the ectopic pregnancy treatment catheter 10A enters the catheter guide 70, a more stable and accurate movement path can be secured. In addition, the catheter guide 70 has a predetermined ductility so that even though the catheter guide 70 enters in vivo and is brought into close contact with other organs of the female body, damage of the organs can be prevented.

The front end part 71 of the catheter guide 70 may be formed as a structure in which it is positioned at a front tip of the catheter guide 70 and can be inserted in vivo through the uterine cervix. The front end part 71 includes an opening portion (not shown) at one end thereof, and the opening portion (not shown) fluidically communicates with the guide through-part 72. The opening portion (not shown) is formed as a structure which is opened so that the ectopic pregnancy treatment catheter 10A can smoothly pass through the catheter guide 70. The diameter of the opening portion (not shown) may be equal to or larger than that of the catheter 10A for treating ectopic pregnancy, but the present invention is not limited thereto. Alternatively, the diameter of the opening portion (not shown) may be smaller that of the ectopic pregnancy treatment catheter 10A. For example, in the case where the diameter of the opening portion (not shown) can be temporarily extended by a given force, it is formed smaller than that of the ectopic pregnancy treatment catheter 10A so that an in-vivo substance can be prevented from being introduced into the catheter guide 70.

Figure 25:
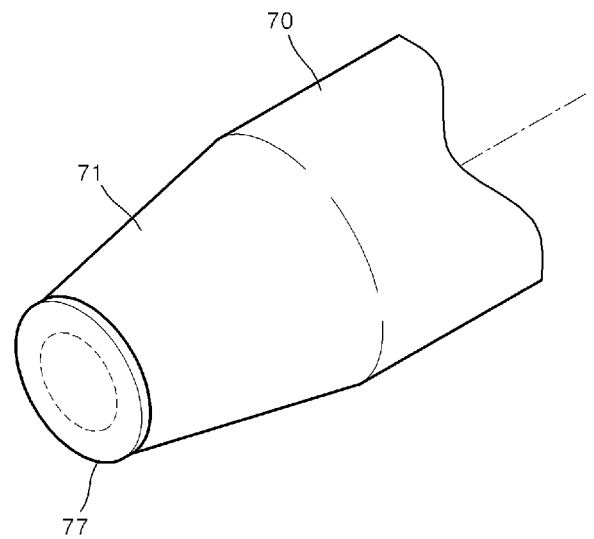
FIG. 25 is a partial perspective view illustrating a state in which a front end part 71 of the catheter guide is closed by a membrane, according to an embodiment of the present invention.
Figure 26:
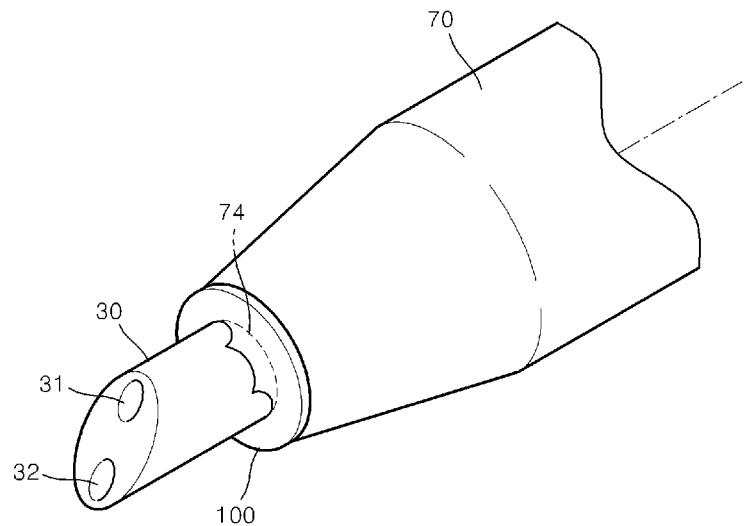
FIG. 26 is a partial perspective view illustrating a state in which a catheter 10a for treating ectopic pregnancy pierces through a membrane 77 and is partially exposed to the outside, according to an embodiment of the present invention.

The front end part 71 may be formed as a structure in which one end thereof has a radius smaller than that of the other end thereof to ensure more smooth in vivo insertion of the catheter guide 70. That is, as shown in FIGS. 24 to 26, the front end part 71 of the catheter guide 70 may be formed to have an inclined face. In this case, the opening portion (not shown) of the front end part 71 may be positioned on the inclined face, but not at the center of the front end part 71.

In addition, the front end part 71 of the catheter guide 70 may be formed as a structure in which it closes the guide through-part 72. FIG. 25 is a partial perspective view illustrating a state in which a front end part 71 of the catheter guide is closed by a membrane, according to an embodiment of the present invention. The front end part 71 to which the present invention is applied may be formed as a structure in which it includes a membrane 77. The front end part 71 is formed as structure in which it is closed by the membrane 77 so that when the catheter guide 70 enters in vivo, an in-vivo substance can be prevented from being introduced into the catheter guide 70. In addition, in the case where the ectopic pregnancy treatment catheter 10A is inserted into the catheter guide 70 and is pushed forwards with a given force, it easily passes through the membrane 77 so that the catheter 10A can penetrate into the gestational sac.

FIG. 26 shows a partial perspective view of a state in which the catheter 10*a* for treating ectopic pregnancy pierces through the membrane 77 and is partially exposed to the outside, according to an embodiment of the present invention.

The membrane 77 may be implemented as a thin film having a predetermined thickness. For example, the membrane 77 may be formed as a thin film which is made of polyamid and has a thickness of from 0.1 μm to 0.3 μm, but the present invention is not limited thereto.

In the meantime, in FIG. 24, the rear end part 73 is positioned at a rear distal end of the catheter guide to serve as an entrance which allows the ectopic pregnancy treatment catheter 10A to enter the inside of the catheter guide 70. Therefore, the rear end part 73 includes an opening portion (not shown) for allowing the ectopic pregnancy treatment catheter 10A to smoothly enter the catheter guide 70, and the opening portion (not shown) also fluidically communicate with the guide through-part 72. In addition, when the catheter guide 70 is inserted in vivo, the rear end part 73 is positioned in vitro so that it also serves as a control knob which allows the catheter guide 70 to reach the gestational sac safely As described above, the description of the catheter guide 70 is merely an embodiment of the present invention, and the present invention is not limited thereto. In other words, various embodiments described with reference to FIGS. 1 to 23 will be able to be applied to suit the catheter guide 70.

It is required that the above-mentioned ectopic pregnancy treatment catheter should be inserted in vivo and directly penetrate into the gestational sac so that the drug is injected into the gestational sac. In addition, it is also required that the catheter guide should be held in position in front of the gestational sac so that the catheter can accurately penetrate into the gestational sac. In the above embodiments, the progress direction of the catheter and the catheter guide could be controlled using the connecting parts 40, 400 and 400*b*, and the control knob 25 of the ectopic pregnancy treatment catheter, or the rear end part 73 of the catheter guide. Hereinafter, a description will be given of various embodiments in which the progress direction of the ectopic pregnancy treatment catheter or the catheter guide can be more precisely controlled.

Figure 27:
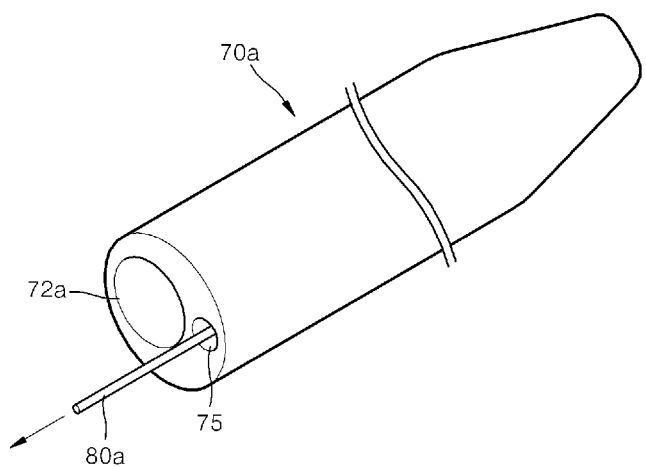
FIG. 27 is a schematic perspective view illustrating a catheter guide enabling adjustment of the progress direction thereof, according to another embodiment of the present invention.
Figure 28:
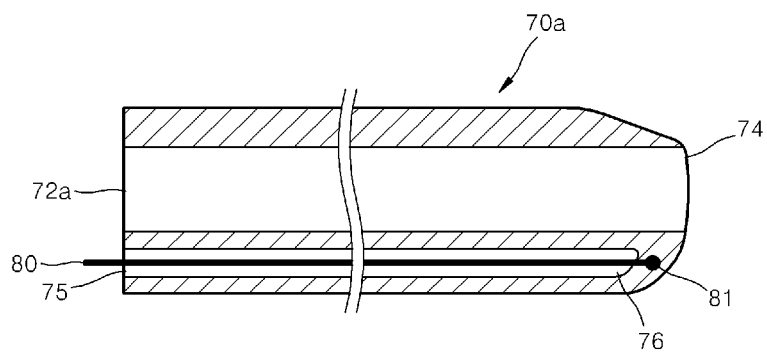
FIG. 28 is a schematic cross-sectional view illustrating the catheter guide of FIG. 27, according to another embodiment of the present invention.

FIG. 27 is a schematic perspective view illustrating a catheter guide enabling adjustment of the progress direction thereof, according to another embodiment of the present invention, and FIG. 28 is a schematic cross-sectional view illustrating the catheter guide of FIG. 27.

In this embodiment, the catheter guide may further include an element for driving the rear end part thereof. For example, the catheter guide 70*a* enabling the control of the progress direction of the catheter may include a guide through-part 72*a*, direction control through-part 75, direction control line 80*a*.

The direction control through-part 75 is formed in the catheter guide 70*a* along the lengthwise direction of the catheter guide 70*a* in such a manner as to be spaced apart from the guide through-part 72*a*.

The direction control line 80*a* is connected at one end thereof to the inside of the direction control through-part 75 and is exposed at the other end thereof to the outside. As shown in FIG. 28, a direction control line fixing member 81 may be disposed at the one end of the direction control line 80*a*. The direction control line fixing member 81 may be formed embeddedly at an inner front end of the direction control through-part 75 in the formation process of the catheter guide 70a. In addition, the other end of the direction control line 80a is a free end, which can be freely adjusted by an operator, and one end of the direction control line 80a can be operated integrally with the front end part of the catheter guide 70a. In addition, the direction control line 80a may be formed as a wire made of a high-strength synthetic resin.

The direction control through-part 75 takes a structure in which it is formed eccentrically to one side from the center of the catheter guide 70a so that a tensile force can be transferred through the direction control line 80a. In this case, the progress direction of the front end part of the catheter guide 70a can be converted to a direction where the direction control line 80a is positioned. The smooth direction conversion of the catheter guide 70a can be performed through only conversion of the front end part of the catheter guide 70a to a predetermined direction due to presence of an entering force of the catheter guide 70a.

In the above embodiment, the direction control line 80a takes a structure in which it is disposed inside the catheter guide 70a, but the present invention is not limited thereto.

Figure 29:
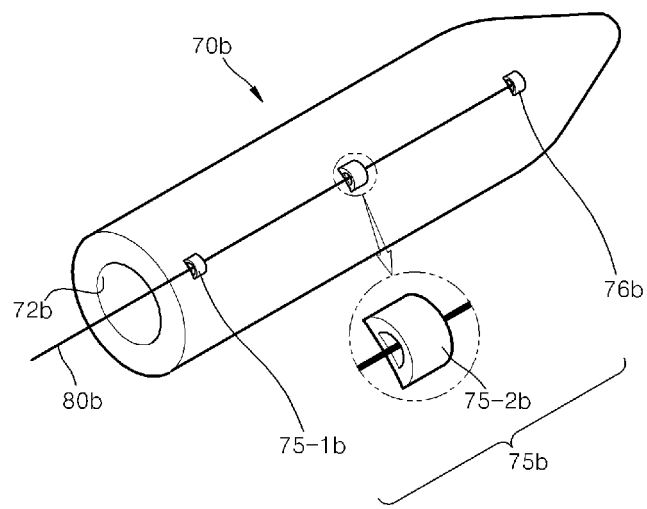
FIG. 29 is a schematic perspective view illustrating a modification of a catheter guide enabling adjustment of the progress direction thereof, according to another embodiment of the present invention.

FIG. 29 is a schematic perspective view illustrating a modification of a catheter guide enabling adjustment of the progress direction thereof, according to another embodiment of the present invention;

As shown in FIG. 29, a catheter guide 70b according to the present invention may include a direction control unit 75b mounted on the outer peripheral surface thereof. The direction control unit 75b is spaced apart from a guide through-part 72b so that it can be disposed on the outer peripheral surface thereof in a lengthwise direction thereof. The direction control unit 75b may include a plurality of direction control line fixing members 75-1b, 75-2b, and 76b.

One end of the direction control line 80b is fixed to only the direction control line fixing member 76b, and the remaining portion of the direction control line 80b is guided to the rear end part of the catheter guide 70b while passing through the direction control line fixing members 75-1b and 75-2b. Likewise, a smoother direction control structure can be implemented by increasing the eccentric position of the direction control line 80b.

According to another embodiment of the present invention, the use of an electrical signal can switch the progress direction of the front end part of the catheter guide.

Figure 30:
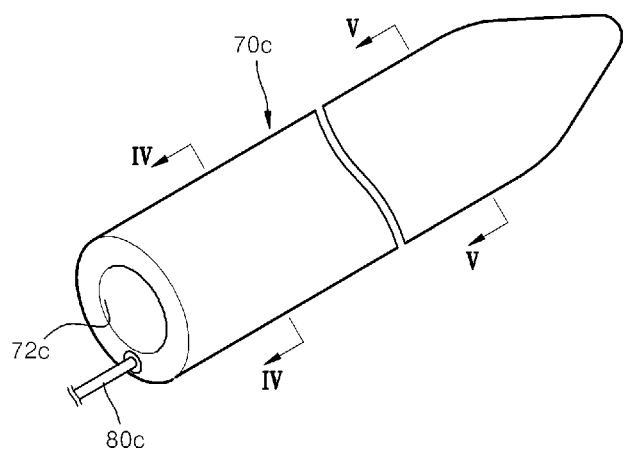
FIG. 30 is a schematic perspective view illustrating another modification of a catheter guide enabling adjustment of the progress direction thereof, according to another embodiment of the present invention.
Figure 31:
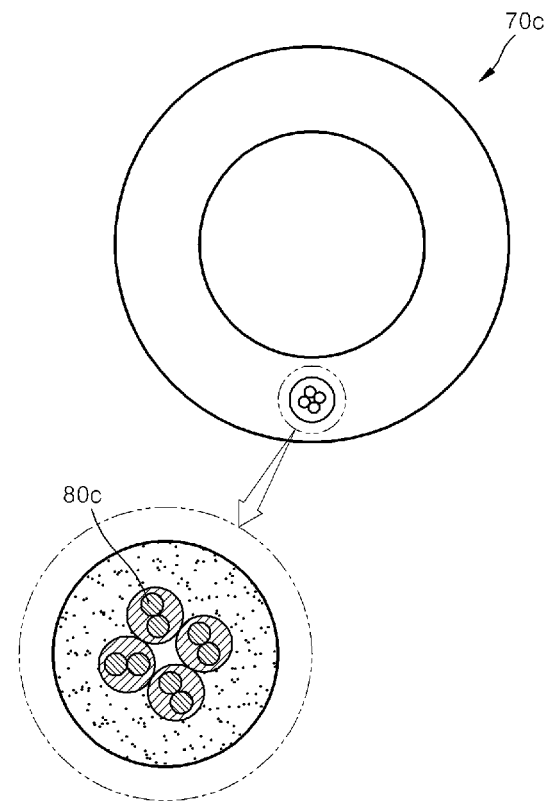
FIG. 31 is a schematic cross-sectional view taken along the line IV-IV of FIG. 30.
Figure 32:
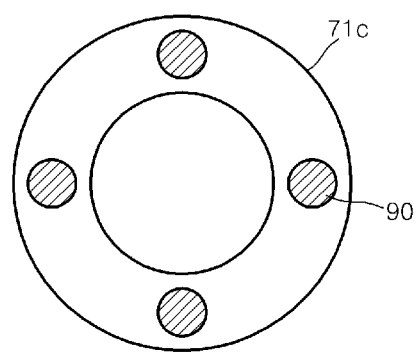
FIG. 32 is a schematic cross-sectional view taken along the line V-V of FIG. 30.
Figure 33:
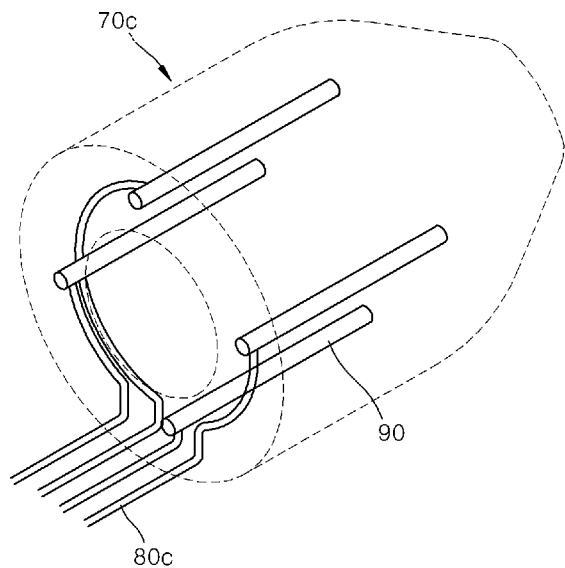
FIG. 33 is a schematic partial perspective view illustrating a direction control unit 90 according to an embodiment of the present invention.

FIG. 30 is a schematic perspective view illustrating another modification of a catheter guide enabling adjustment of the progress direction thereof, according to another embodiment of the present invention, FIG. 31 is a schematic cross-sectional view taken along the line IV-IV of FIG. 30, and FIG. 32 is a schematic cross-sectional view taken along the line V-V of FIG. 30, and FIG. 33 is a schematic partial perspective view illustrating a direction control unit 90 according to an embodiment of the present invention.

Referring to FIGS. 30 to 32, a catheter guide 70c according to the present invention may include a direction control line 80c and a direction control unit 90. Also, referring to FIG. 33, the direction control line 80c may be implemented as a plurality of electrical signal lines, each of which is connected to an associated one of a plurality of direction control units 90. The direction control lines 80c may be formed embedded in the catheter guide 70c.

The direction control units 90 may be disposed inside the catheter guide 70c along a lengthwise direction of the catheter guide 70c in such a manner as to be spaced apart from the guide through-part 72c by a predetermined distance. In addition, the direction control unit 90 may contain a shape memory alloy. For example, when predetermined electrical signals are applied to the direction control units 90 through the direction control lines 80c, the direction control units 90 generate heat. The direction control unit 90 formed of the shape memory alloy is deformed into a preset shape so that the progress direction of the front end part of the catheter guide 70c can be switched.

In addition, at least one direction control unit 90 may be disposed at the front end part of the catheter guide 70c. In this embodiment, the catheter guide takes a structure in which four direction control units 90 are equiangularly circumferentially arranged axially extending in such a manner as to be spaced apart from the guide through-part of the catheter guide 70c by a predetermined distance, but the present invention is not limited thereto and may take a structure enabling a multidirectional operation. The direction control units 90 and the direction control lines 80c may be formed as a structure in which they are injection-molded while being embedded in the catheter guide 70c.

Figure 34:
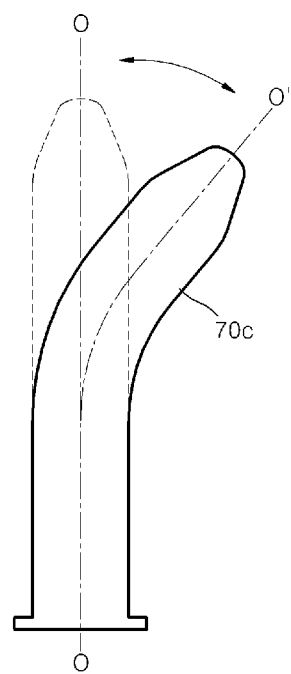
FIG. 34 is a schematic view illustrating an operational state of a catheter guide according to an embodiment of the present invention.

FIG. 34 is a schematic view illustrating an operational state of a catheter guide according to an embodiment of the present invention;

As shown in FIG. 34, when an electrical signal is applied to any one of the four direction control units 90, the catheter guide 70c can be moved from a central line (O-O) as a neural state before application of the electrical signal to a central line (O-O) as a movable state. For example, as shown in FIG. 34, in the case where the front end part of the catheter guide 70c is moved to the right, the catheter guide 70c or the ectopic pregnancy treatment catheter is maintained in a predetermined curved state in vivo so that the catheter guide 70c or the ectopic pregnancy treatment catheter can be moved to the gestational sac in a safer and more accurate manner.

Figure 35:
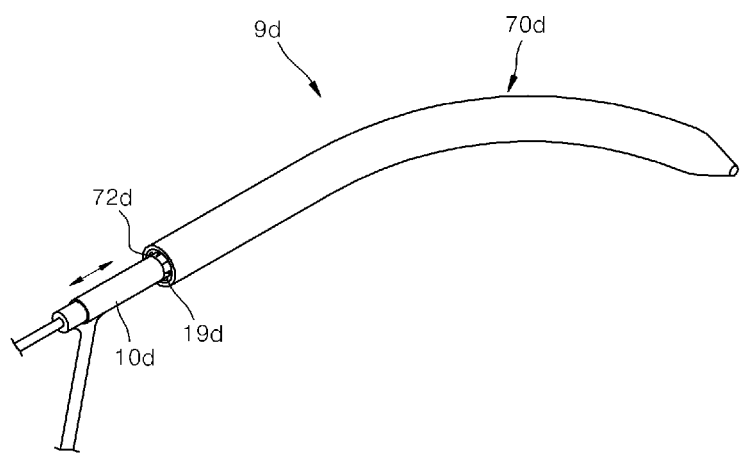
FIG. 35 is a schematic perspective view illustrating another modification of a catheter unit for treating ectopic pregnancy according to another embodiment of the present invention.

FIG. 35 is a schematic perspective view illustrating another modification of a catheter unit for treating ectopic pregnancy according to another embodiment of the present invention.

The ectopic pregnancy treatment catheter according to an embodiment of the present invention may further include another element for smooth movement thereof. For example, as shown in FIG. 35, a catheter 10d for treating ectopic pregnancy may further include a guide projection 19b for enabling the stable movement in the catheter guide 70d. The catheter 10d for treating ectopic pregnancy can be moved inside the guide through-part 72d of the catheter guide 70d. In this case, when the catheter guide 70d enters in vivo, a body fluid may be introduced into the guide through-part 72d. For this reason, the outer peripheral surface of the catheter 10d and the inner peripheral surface of the guide through-part 72d are brought into tight contact with each other due to the surface tension caused by the introduced body fluid, and thus smooth adjustment of the catheter with respect to the catheter guide may be difficult. Therefore, in the present invention, the guide projection 19b is formed on the outer peripheral surface of the catheter 10d for treating ectopic pregnancy to that the outer peripheral surface of the catheter 10d can be prevented from being brought into tight contact with the inner peripheral surface of the guide through-part 72d.

Figure 36:
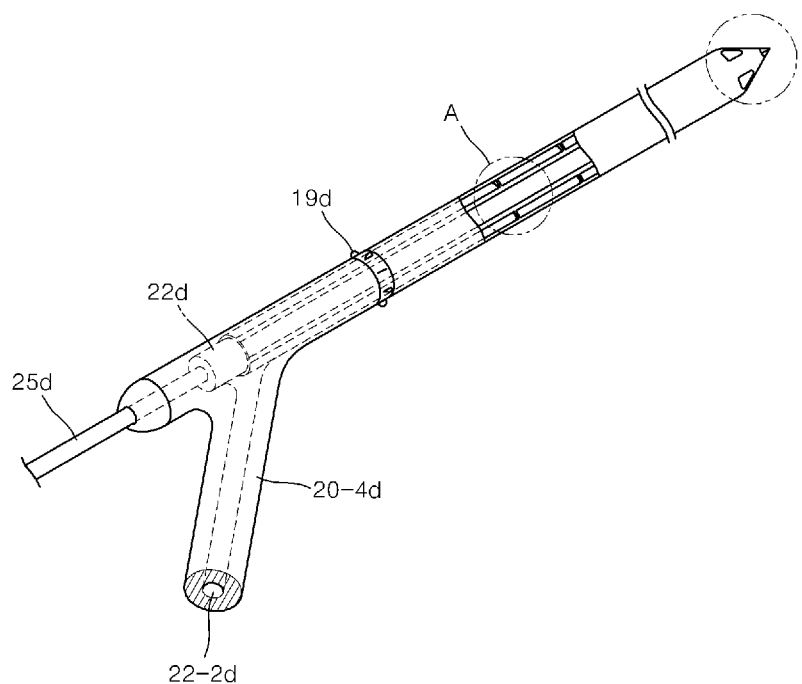
FIG. 36 is a schematic perspective view illustrating a catheter unit for treating ectopic pregnancy of FIG. 35, according to another embodiment of the present invention.
Figure 37:
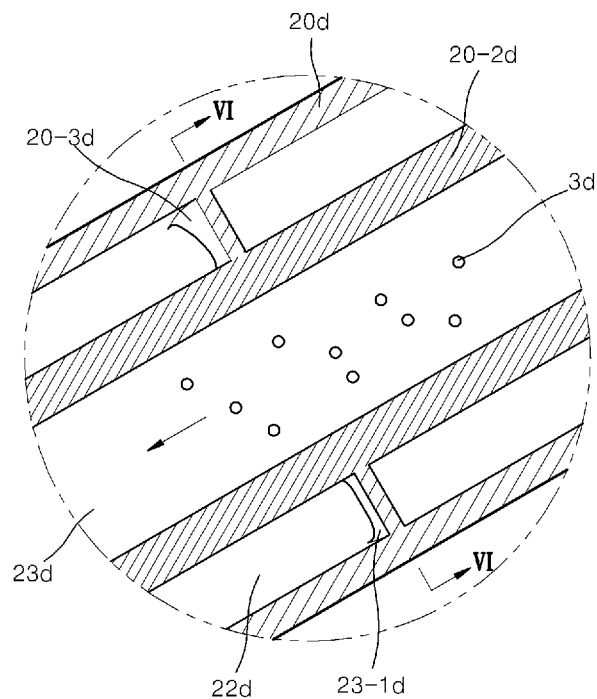
FIG. 37 is a partially enlarged perspective cross-sectional view illustrating a portion A of FIG. 36.
Figure 38:
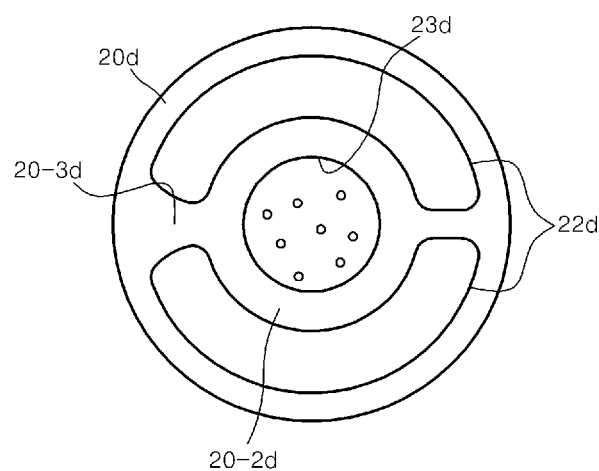
FIG. 38 is a partial cross-section view taken along the line VI-VI of FIG. 37.
Figure 39:
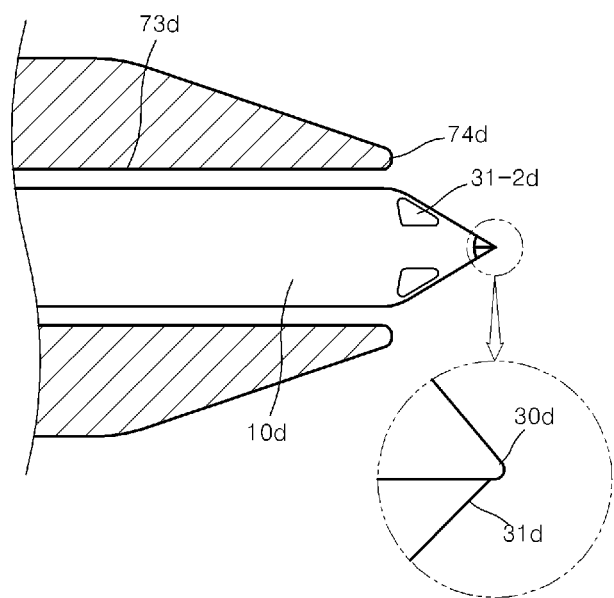
FIG. 39 is a partially enlarged view illustrating a front end part of FIG. 36

FIG. 36 is a schematic perspective view illustrating a catheter unit for treating ectopic pregnancy of FIG. 35, according to another embodiment of the present invention, FIG. 37 is a partially enlarged perspective cross-sectional view illustrating a portion A of FIG. 36, FIG. 38 is a partial cross-section view taken along the line VI-VI of FIG. 37, and FIG. 39 is a partially enlarged view illustrating a front end part of FIG. 36.

A catheter 10*d* for treating ectopic pregnancy according to the present invention may be formed as a double-pipe structure. For example, as shown in FIGS. 35 to 39, a catheter body part 20*d* is implemented as a hollow type and may further include a catheter inner body part 20-2*d* formed therein. The catheter inner body part 20-2*d* is formed as a hollow tube structure, and the catheter inner body part 20-2*d* and the catheter body part 20*d* are connected to each other by means of a support bridge 20-3*d*. Referring to FIG. 37, a plurality of support bridges 20-3*d* may be disposed spaced apart from each other at uniform intervals along a lengthwise direction of the catheter body part 20*d*. Alternatively, the support bridges 20-3*d* may take a structure in which they are formed continuously in the lengthwise direction of the catheter body part 20*d*.

Likewise, a space defined between the catheter body part 20*d* and the catheter inner body part 20-2*d* may be formed as a catheter injection through-hole 22*d*, and the internal space defined by the catheter inner body part 20-2*d* may be formed as a catheter suction through-hole 23*d*. In other words, by virtue of the double-pipe structure, the catheter injection through-hole 22*d* and the catheter suction through-hole 23*d* are formed in the same direction along the lengthwise direction of the catheter body part 20*d*, but they may take a structure of being disposed concentrically. It has been illustrated in this embodiment that the catheter suction through-hole 23*d* is formed inside the catheter inner body part 20-2*d*, but a vice-versa case may also be implemented as an embodiment of the present invention.

In addition, as shown in FIGS. 35 and 36, a catheter 10*d* for treating ectopic pregnancy according to the present invention may further include a catheter body branched part 20-4*d* branched off from the catheter body part 20*d* in a "Y" shape. The catheter body branched part 20-4*d* includes a catheter injection-extending through-hole 22-2*d* formed therein. The catheter injection-extending through-hole 22-2*d* may take a structure in which it fluidically communicates with the catheter injection through-hole 22*d* so that a smooth connection between the catheter and the suction device (not shown)/the injection device (not shown) can be established.

In addition, referring to FIG. 39, the catheter 10*d* for treating ectopic pregnancy having a double-pipe structure may include flow passage parts 31*d* and 31-2*d* formed at the front end part thereof. The flow passage part 31*d* can fluidically communicate with the catheter suction-extending through-hole 23*d* formed at the center of the catheter body part, and the flow passage part 31-2*d* formed on the inclined face can fluidically communicate with the catheter injection-extending through-hole 22*d* formed between the double tubes. The flow passage part 31*d* takes a structure in which it is formed only in a half size at the front tip end of the catheter front end part so that the catheter 10*d* can smoothly penetrate into the gestational sac.

Figure 40:
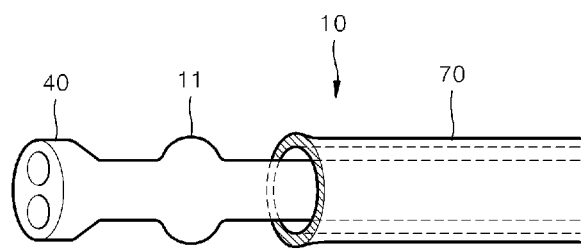
FIG. 40 is a schematic perspective view illustrating a catheter for treating ectopic pregnancy, which can be prevented from being inserted into a catheter guide, according to another embodiment of the present invention.

FIG. 40 is a schematic perspective view illustrating a catheter for treating ectopic pregnancy, which can be prevented from being inserted into a catheter guide, according to another embodiment of the present invention;

An ectopic pregnancy treatment catheter 10 according to the present invention can prevent the ectopic pregnancy treatment catheter from piercing through the gestational sac to injure other bodily sites inside the female body during the procedure. Referring to FIG. 40, the ectopic pregnancy treatment catheter 10 may further include an insertion preventing part 11 formed on the outer peripheral surface thereof so as to prevent the ectopic pregnancy treatment catheter 10 from further entering the catheter guide 7.0

It has been illustrated in FIG. 40 that the insertion preventing part 11 is protruded outwardly from the outer peripheral surface thereof, but the present invention is not limited thereto and may be implemented in various manners. For example, the ectopic pregnancy treatment catheter 10 can prevent the ectopic pregnancy treatment catheter 10 from being inserted into the catheter guide 70 as long as at least one projection is formed on the outer peripheral surface of the ectopic pregnancy treatment catheter 10.

In addition, the insertion preventing part 11 may be formed integrally with the ectopic pregnancy treatment catheter 10, but the present invention is not limited thereto. For example, the insertion preventing part 11 may be formed as a structure in which it is configured in an engageable ring type so that it can en engaged with the ectopic pregnancy treatment catheter 10. In this case, an operator checks the length of the ectopic pregnancy treatment catheter 10 necessary for a patient using an ultrasonic device, and then engages the insertion preventing part 11 with the ectopic pregnancy treatment catheter 10 so that the ectopic pregnancy treatment catheter can be avoided from piercing through the gestational sac.

Meanwhile, it has been described in the above embodiments that the catheter guide is formed as a single piece, but the catheter guide according to the present invention may take a nested arrangement structure.

Figure 41:
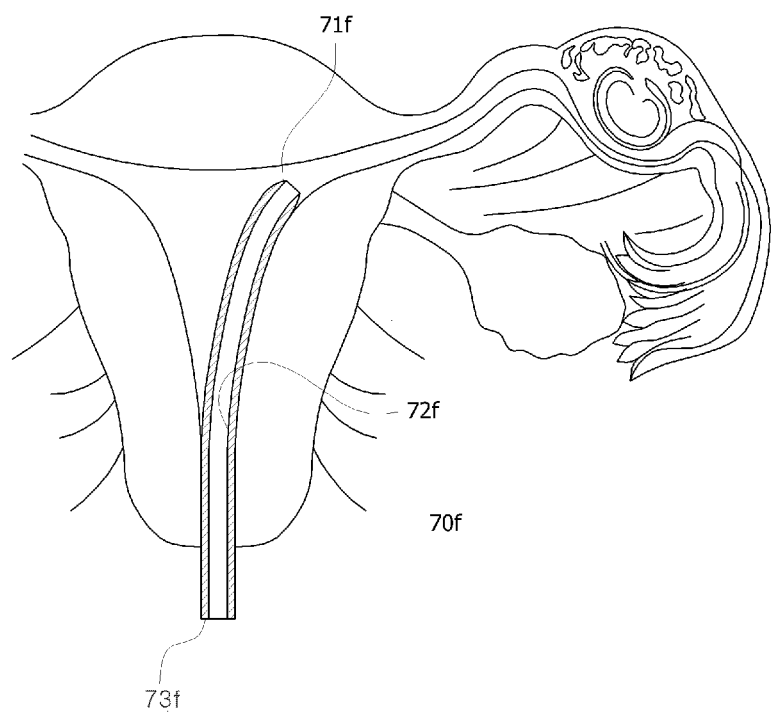
FIGS. 41 to 43 are schematic views illustrating a state in which a catheter guide for treating ectopic pregnancy is in use according to another embodiment of the present invention.
Figure 42:
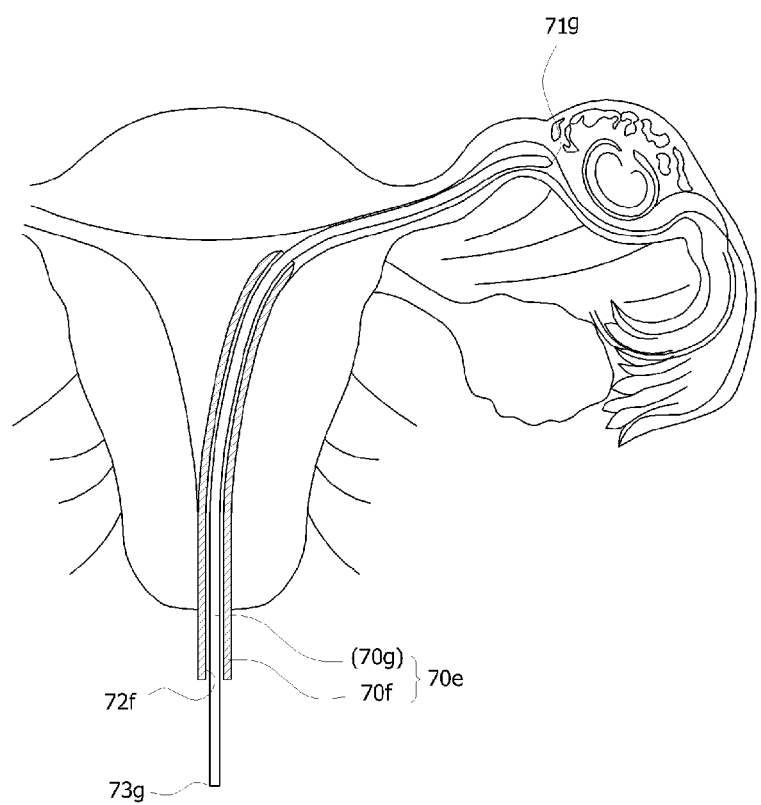
Figure 43:
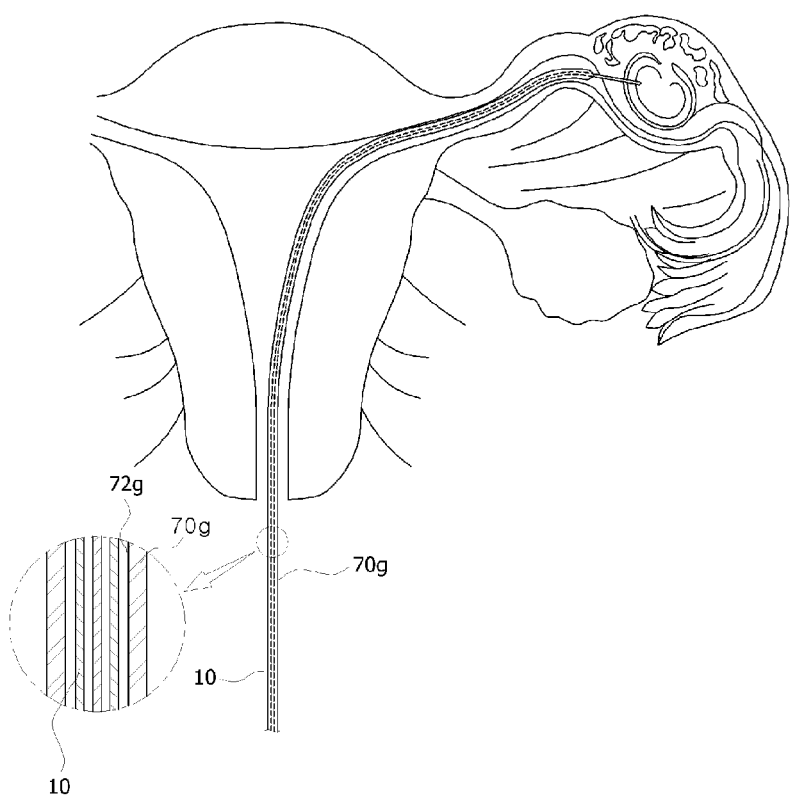

FIGS. 41 to 43 are schematic views illustrating a state in which a catheter guide for treating ectopic pregnancy is in use according to another embodiment of the present invention.

FIG. 41 shows a state in which a first catheter guide has entered the uterus through a vaginal cavity, FIG. 42 shows a state in which the first catheter guide is penetratingly disposed in a second catheter guide, which is positioned close to the gestational sac, FIG. 43 shows a state in which an ectopic pregnancy treatment catheter penetratingly disposed in the second catheter guide penetrates into the gestational sac and performs the medial treatment of ectopic pregnancy.

In FIGS. 41 to 43, the ectopic pregnancy treatment catheter guides 70*e*; 70*f* and 70*g* are inserted at one ends thereof into the female body and are exposed at the other ends thereof to the outside of the female body. In this case, the catheter guides have a preset stiffness or rigidity so that the axial lines thereof form a predetermined curved structure along the lengthwise direction of the catheter guides. Herein, the axial line indicates a segment of the lengthwise direction at the center of the catheter guide (see the central line O-O of FIG. 24). The ectopic pregnancy treatment catheter guides 70*e*, 70*f* and 70*g* may constitute a nested double catheter guide structure including a first catheter guide 70*f* and a second catheter guide 70*g*. Of course, the first catheter guide 70*f* and the second catheter guide 70*g* may be used independently of each other, if necessary.

The first catheter guide 70*f* may include a first front end part 71*f*, a first through-part 72*f*, and a first rear end part 73*f*. The first catheter guide 70*f* may be implemented in a tubular shape. The first catheter guide 70*f* includes the first front end part 71*f* at one end thereof and the first rear end part 73*f* at the other end thereof.

The first front end part 71*f* of the first catheter guide 70*f* is formed as a structure in which it is introduced in vivo through the vaginal cavity, and is positioned in proximity of an entrance of the fallopian tube. The first through-part 72*f* of the first catheter guide 70*f* is formed as a structure in which the first catheter guide 70f is passed therethrough along the lengthwise direction of the first catheter guide 70f. In addition, the first rear end part 73f of the first catheter guide 70f may have a structure in which the second catheter guide 70g and/or the ectopic pregnancy treatment catheter guide can enter the first through-part 72f through first rear end part 73f and can be moved through the first through-part 72f.

The first catheter guide 70f is formed to have a predetermined curved structure, i.e., a preset radius of curvature and is made of a material having a predetermined stiffness or rigidity and ductility. For example, the first catheter guide 70f may be formed of a material such as silicon, polyethylene, or the like. Stiffness or rigidity of the first catheter guide 70f may be formed in consideration of the properties of the material itself, and the first catheter guide 70f may take a structure in which it has stiffness or rigidity formed in consideration of the thickness thereof. Herein, the first catheter guide 70f may be formed to have stiffness or rigidity including an elastic force enabling the first catheter guide 70f to return to its original position to form a predetermined curved structure in the case where an external force is removed while having sufficient ductility allowing for slight deformation of the first catheter guide 70f in the process of introducing the first catheter guide 70f into the female body through the vaginal cavity.

The second catheter guide 70g may include a second front end part 71g, a second through-part 72g, and a second rear end part 73g. The second catheter guide 70g may take a structure in which it is movably penetratingly disposed inside the first catheter guide 70f, and is inserted at one end thereof into the fallopian tube along first catheter guide 70f and is exposed at the other end thereof to the outside of the female body so that the ectopic pregnancy treatment catheter can be passed through the second catheter guide 70g. The second catheter guide 70g includes the second front end part 71g at one end thereof and the second rear end part 73g at the other end thereof. The second catheter guide 70g may include the second through-part 72g formed therein along the lengthwise direction thereof. In this case, the second catheter guide 70g is introduced into the first through-part 72f of the first catheter guide 70f to cause the second front end part 71g to penetrate into the fallopian tube through the first front end part 71f and the second rear end part 73g to be exposed to the outside so that the ectopic pregnancy treatment catheter can be inserted into the second rear end part 73g by an operator. The ectopic pregnancy treatment catheter inserted into the second catheter guide can reach in proximity of the gestational sac safely, and the medical procedures including penetration of the catheter into the gestational sac in the fallopian tube, suction of the amniotic fluid, and injection of the drug can be performed on ectopic pregnancy.

In the meantime, the ectopic pregnancy treatment catheter guide 70e according to this embodiment takes a double nested tube structure so that the medical procedures can be performed in a more accurate and stable manner. An example of the medical procedures which can be used the present invention will be described hereinafter. In other words, as shown in FIGS. 41 to 43, the first catheter guide 70f is inserted in vivo and the first front end part 71f is positioned in proximity of the fallopian tube owing to the predetermined stiffness or rigidity and the curved structure thereof. Thereafter, an operator inserts the second catheter guide 70g into the first through-part 72f through the first rear end part 73f. The second catheter guide 70g passes through the first front end part 71f of the first catheter guide 70f and penetrates into the fallopian tube. The second catheter guide 70g has a diameter smaller than that of the first catheter guide 70f and is made of a material having ductility, and thus it takes a structure in which the second catheter guide 70g can be deformed along the first curved through-part 72f of the first catheter guide 70f. Thus, the second catheter guide 70g is smoothly positioned insertedly in front of the fallopian tube. The second front end part 71g of the second catheter guide 70g is positioned in front of the gestational sac to induce the ectopic pregnancy treatment catheter 10 to safely reach the gestational sac.

Thereafter, when the ectopic pregnancy treatment catheter 10 is positioned in proximity of the gestational sac through the second catheter guide 70g, it penetrates into the gestational sac so that the amniotic fluid suction process and/or the drug injection process can be performed. More specifically, the ectopic pregnancy treatment catheter 10 is inserted into the second catheter guide 70g through the second rear end part 73g, safely enters a position in proximity of the gestational sac through the second through-part 72g, and penetrates into the gestational sac through the second front end part 71g. The second front end part 71g is positioned in proximity of the gestational sac, and thus the ectopic pregnancy treatment catheter 10 can safely penetrate into the gestational sac. After the ectopic pregnancy treatment catheter 10 penetrates into the gestational sac, it suctions the amniotic fluid in the gestational sac through the amniotic fluid suction tool connected to the ectopic pregnancy treatment catheter 10 and injects a given drug into the gestational sac through the drug injection tool connected to the ectopic pregnancy treatment catheter 10 so that ectopic pregnancy can be treated safely and promptly. Then, the ectopic pregnancy treatment catheter, second catheter guide and/or first catheter guide, which has been inserted in vivo are removed the female body. Herein, the order or selection of the amniotic fluid suction and/or the drug injecting can be controlled properly depending on the therapeutic environment, and the removal order of the ectopic pregnancy treatment catheter and the first and second catheter guides can also be controlled the therapeutic environment.

Meanwhile, in order to reduce an unpleasant sensation of a patient and smoothly perform the medical procedures, as shown in FIGS. 42 to 43, the first catheter guide 70f is removed from the patient body and then the medical procedures may be performed only through the ectopic pregnancy treatment catheter 10. The first catheter guide 70f may be removed after insertion of the second catheter guide 70g into the fallopian tube. The medical procedures can be performed selectively, including insertion/removal of the ectopic pregnancy treatment catheter 10 into/from the second catheter guide 70g depending on the proper therapeutic environment and conditions so that the curved structure can be smoothly maintained to complete the smooth insertion of the ectopic pregnancy treatment catheter 10. Of course, various medical procedures may be selected such as performing the treatment in a state of maintaining the first catheter guide depending on the state of the patient and the like.

Figure 44:
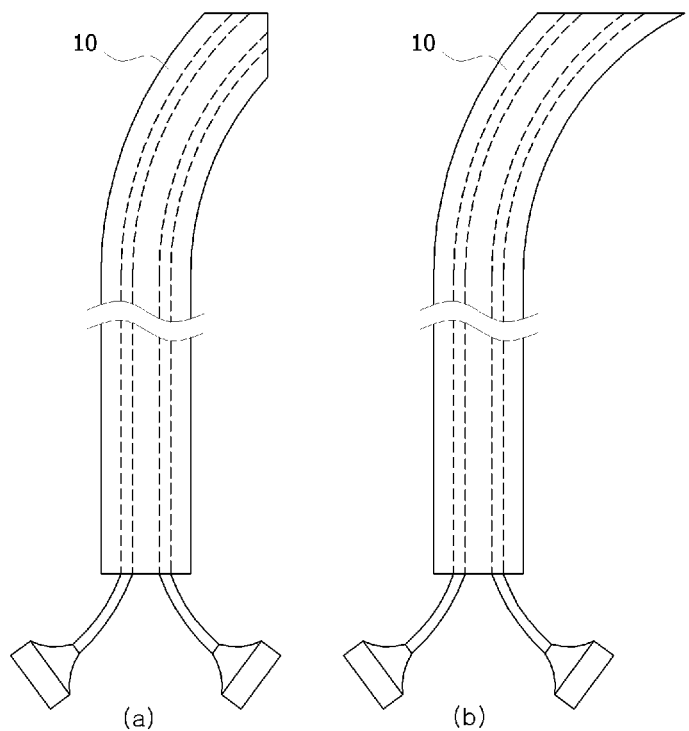
FIG. 44 is a schematic perspective view illustrating a catheter for treating ectopic pregnancy used in the catheter guide for treating ectopic pregnancy of FIGS. 41 to 43.

FIG. 44 is a schematic view illustrating a state in which ectopic pregnancy treatment catheter 10 is inserted into the ectopic pregnancy treatment catheter guide 70e. The structures of the catheter 10 and the catheter guide 70e in this embodiment are the same as those described in the above embodiments. In case of FIGS. 44(a) and 44(b), the penetrating part formed at the front end of the ectopic pregnancy treatment catheter 10 may take a conical shape (see FIG. 44(a)) or a truncated shape cut in one direction (see FIG. 44(b)). Likewise, a proper structure of the ectopic pregnancy treatment catheter 10 may be selected depending on the state of the patient and the therapeutic environment.

In the above embodiment, although the ectopic pregnancy treatment catheter guide has been described centering on the double nested arrangement structure, a description may be given of the case where the ectopic pregnancy treatment catheter guide further includes a third catheter guide or a fourth catheter guide, which is interposed and inserted between the first catheter guide and the second catheter guide, if necessary. In other words, the ectopic pregnancy treatment catheter guide may be implemented in various modified manners depending on the use environment and needs, such as being implemented as a multi-nested arrangement structure.

Figure 45:
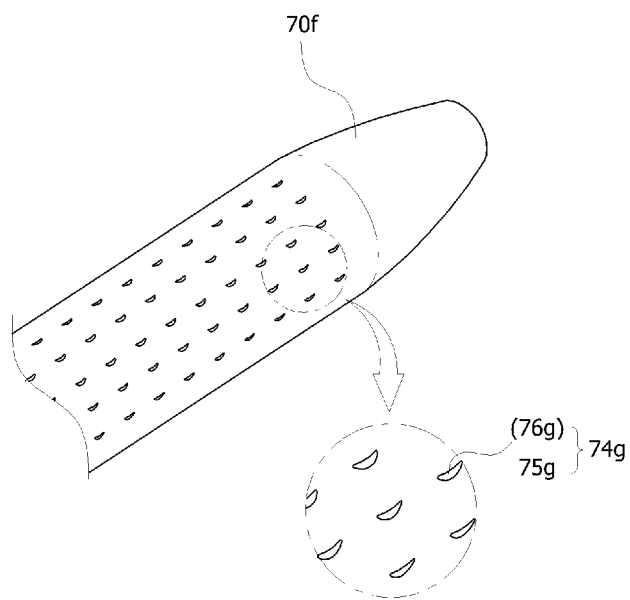
FIGS. 45 and 46 are partially enlarged views illustrating a modification of the catheter guide for treating ectopic pregnancy of FIGS. 41 to 43 according to another embodiment of the present invention.
Figure 46:
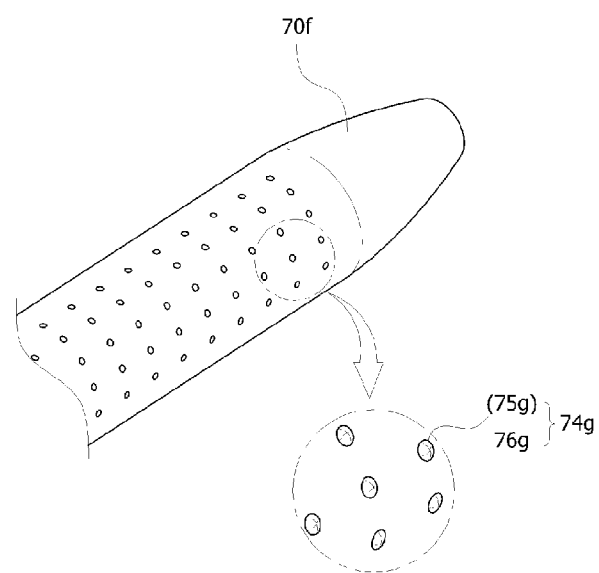

In the meantime, the ectopic pregnancy treatment catheter guides 70e, 70f and 70g of the present invention take a double-nested through structure, but may further include an element for preventing resistance by the close contact between the first catheter guide and the second catheter guide during a relative through movement therebetween. In other words, the first catheter guide 70f has a preset radius of curvature and the second catheter guide 70g has a ductility larger than that of the first catheter guide 70f. Thus, the second catheter guide 70g has a surface-processed part 74g thereon to prevent the second catheter guide 70g from being not smoothly inserted into the first through-part 72f due to surface tension by a liquid such as a body fluid in the process in which the second catheter guide 70g is moved along the first through-part 72f while passing through the first through-part 72f. As show in FIGS. 45 and 46, the surface-processed part 74g is formed on the outer peripheral surface of the second catheter guide 70g. The surface-processed part 74g may include a surface-processed part 75g having a recessed pattern or a surface-processed part 76g having a projected pattern. Likewise, by virtue of the surface-processed parts (74g; 75g and 76g), the second catheter guide 70g may have a structure in which the surface tension by the liquid interposed between two contact surfaces of the second catheter guide 70g and the first catheter guide 70f is minimized to minimize the relative movement resistance between the first and second catheter guides in the process in which the second catheter guide 70g is moved along the first through-part 72f while passing through the first through-part 72f. In addition, the surface-processed part may be implemented in various modified manners, including being formed on the entire outer peripheral surface of the second catheter guide or being formed limitedly on a specific region of the outer peripheral surface of the second catheter guide, if necessary.

As described above, the present invention can provide the ectopic pregnancy treatment catheter, the catheter guide and the ectopic pregnancy treatment catheter unit including the catheter and the catheter guide. The embodiments thereof may include the following characteristics.

For example, the surface of the ectopic pregnancy treatment catheter and catheter guide is wholly or partially coated with a material which can be identified by an imaging apparatus so that the imaging apparatus can identify whether or not the pregnancy treatment catheter and the catheter guide reach the gestational sac accurately. For example, examples of the imaging apparatus include an ultrasonic device, an X-ray imaging apparatus, an X-ray computer tomographic (CT) imaging apparatus, and a magnetic resonance imaging (MRI) apparatus.

In another embodiment, the ectopic pregnancy treatment catheter and catheter guide according to the present invention may be coated with a material which can be identified by an imaging apparatus. Therefore, even if the ectopic pregnancy treatment catheter or the catheter guide is inserted in vivo without separate identification markings, such identification can be made by the imaging apparatus.

In another embodiment, the ectopic pregnancy treatment catheter and catheter guide according to the present invention may include an identifier formed on the outer peripheral surface thereof so as to indicate the length thereof. For example, the identifier capable of indicating the length may be displayed in the form of scales, figures, colors or materials. In addition, the identifier capable of indicating the length may be displayed either on one end of the ectopic pregnancy treatment catheter and catheter guide being inserted or on the other end thereof exposed to the outside.

In another embodiment, in the case where the imaging apparatus cannot be used in the treatment of ectopic pregnancy, the length of the ectopic pregnancy treatment catheter and catheter guide necessary for a patient is first measured using the imaging apparatus and then a scale displayed on the outer peripheral surface of the catheter and catheter guide is checked so that ectopic pregnancy can be treated.

In another embodiment, a scale can be displayed on the outer surface of the ectopic pregnancy treatment catheter and catheter guide to check the depth of the ectopic pregnancy treatment catheter or the catheter guide actually inserted in vivo or determine the depth of the ectopic pregnancy treatment catheter or the catheter guide, which is to be inserted in vivo. When the ectopic pregnancy treatment catheter and catheter guide collides against the wall of in vivo organs during its in vivo insertion, the in vivo organs are injured as well as a patient can feel an unpleasant sensation. Thus, the use of the above treatment method can perform the treatment of ectopic pregnancy in a safer and more efficient manner.

In addition, the ectopic pregnancy treatment catheter and catheter guide according to the present invention as shown in FIGS. 1 to 46 has a certain non-flexibility while being formed of a flexible material, and thus can reach a desired in vivo targeting site promptly and accurately without injuring the vessel wall during its in vivo insertion.

In addition, since the ectopic pregnancy treatment catheter according to the present invention is implemented in the form of a fine tube, it may be formed of a material having a predetermined stiffness or rigidity, which can endure a given pressure to prevent the shape change due to the pressure applied thereto during the amniotic fluid suction or the drug injection.

The aforementioned embodiments are merely examples, and the present invention is not limited thereto. For example, the ectopic pregnancy treatment catheter and catheter guide of the present invention can be used in the medical treatment by alternative selection or combination depending therapeutic environments. An ectopic pregnancy treatment catheter and a catheter guide, i.e., any one selected from the first catheter guide and the second catheter guide can be used in the treatment of ectopic pregnancy. After one catheter guide is inserted into the fallopian tube through the vaginal cavity and the front end port thereof is positioned in proximity of the gestational sac, the ectopic pregnancy treatment catheter can be stably guided to the gestational sac while passing through the catheter guide. Thereafter, the penetrating part of the ectopic pregnancy treatment catheter penetrates into the gestational sac, and the treatment procedures can be performed which include suction of the amniotic fluid in the gestational sac and injection of the drug using the external syringe tool connected to the catheter. In addition, the ectopic pregnancy treatment catheter may be used alone without a separate catheter guide, if necessary. In other words, the ectopic pregnancy treatment catheter is inserted into the fallopian tube through the vaginal cavity, and then directly penetrates into the gestational sac so that the medical treatment through the amniotic fluid suction and the drug injection can be performed. Consequently, the treatment procedures can be selected variously depending on therapeutic environments.

Various characteristics of the embodiments described with reference to FIGS. 1 to 46 can be combined with each other. In addition, the embodiments as described above are merely illustrative and the invention is not limited to these embodiments. It will be appreciated by a person having an ordinary skill in the art that various equivalent modifications and variations of the embodiments can be made without departing from the spirit and scope of the present invention. Therefore, the true technical scope of the present invention should be defined by the technical spirit of the appended claims.

INDUSTRIAL APPLICABILITY

The present invention can be used variously as a therapeutic unit for removing a body fluid through in vivo invasion or penetration besides the treatment of ectopic pregnancy.

The invention claimed is:

1. A catheter unit having a catheter for treating ectopic pregnancy and a catheter guide for treating ectopic pregnancy, which is inserted at one end thereof into a fallopian tube through a vaginal cavity and is exposed at the other end thereof to the outside of a female body, the catheter guide having a catheter through-part configured to be inserted at one end thereof into the fallopian tube through the vaginal cavity and exposed at the other end thereof to the outside of the female body, the catheter through-part comprising a through-line through which the catheter is allowed to pass, wherein the catheter comprises:

at least one flow passage part configured to form a flow passage along which liquid is introduced into the catheter through the one end or the other end of the catheter;

a penetrating part connected to the one end of the catheter and including a front tip end for penetrating into a gestational sac; and a connecting part connected to the other end of the catheter and configured to be coupled to at least one syringe tool for injecting or suctioning the liquid, wherein the catheter is formed as a double-pipe structure, wherein the catheter guide includes:

a direction control line being used to control the progress direction of the catheter; and direction control units being disposed on the outer peripheral surface of the catheter guide along a lengthwise direction of the catheter guide in such a manner as to be spaced apart from a guide through-part of the catheter guide by a predetermined distance, and wherein one end of the direction control line is fixed to one of the direction control units, and the direction control line is guided by at least one of the others of the direction control units along the lengthwise direction of the catheter guide.

2. The catheter unit according to claim 1, wherein the syringe tool comprises at least one of a drug injection tool configured to inject a drug into the gestational sac and an amniotic fluid suction tool configured to suction an amniotic fluid in the gestational sac.

3. The catheter unit according to claim 1, wherein the connecting part comprises at least one of an introducing opening portion and a discharging opening portion, the introducing opening portion being configured to allow the drug which is to be delivered into the gestational sac to be introduced into the flow passage part from the syringe tool therethrough, the discharging opening portion being configured to allow the amniotic fluid in the gestational sac to be discharged to the syringe tool therethrough.

4. The catheter unit according to claim 3, wherein the connecting part comprises a first connecting part including the introducing opening portion and a second connecting part including the discharging opening portion, the first connecting part and the second connecting part being configured to be branched off from each other.

5. The catheter unit according to claim 1, wherein the connecting part is configured as a separate member so that it is allowed to be engaged with and disengaged from the catheter for treating ectopic pregnancy.

6. The catheter unit according to claim 5, wherein one end of the connecting part it is detachably connected to a distal end of the catheter for treating ectopic pregnancy so as to allow the one end to fluidically communicate with the flow passage part, and the other end of the connecting part includes a diameter enough to be capable of being connected to the syringe tool.

7. The catheter unit according to claim 1, wherein the penetrating part comprises at least one of a first opening portion configured to allow the drug introduced into the flow passage part from the syringe tool to be discharged to the gestational sac therethrough, and a second opening portion configured to allow the amniotic fluid in the gestational sac to be introduced into the flow passage part therethrough.

8. The catheter unit according to claim 7, wherein the penetrating part is formed to have an inclined face formed at a predetermined angle, and at least one of the first opening portion and the second opening portion is formed on the inclined face.

9. The catheter unit according to claim 1, wherein the connecting part further comprised a direction control unit configured to adjust the progress direction of the catheter for treating ectopic pregnancy.

10. The catheter unit according to claim 1, wherein the catheter guide comprises:

a first opening portion formed at one end of the catheter through-part so that the catheter for treating ectopic pregnancy is allowed to exit the first opening portion;

a second opening portion formed at the other end of the catheter through-part so that the catheter for treating ectopic pregnancy is allowed to enter the second opening portion, wherein the catheter through-part interconnects the first opening portion and the second opening portion, and includes a radius of curvature which is preset along the lengthwise direction thereof.

11. The catheter unit according to claim 10, wherein the catheter through-part comprises a membrane disposed at the one end thereof, the membrane being configured to close the first opening portion, whereby the membrane is allowed to be ruptured by a penetrating part of the catheter for treating ectopic pregnancy.

12. The catheter unit according to claim 10, wherein the catheter for treating ectopic pregnancy comprises:

a flow passage part configured to form a flow passage of a liquid;

a penetrating part including a front tip end for penetrating into a gestational sac;

a connecting part connected to a syringe tool comprising at least one of a drug injection tool configured to inject a drug into the gestational sac through the flow passage part and an amniotic fluid suction tool configured to suction an amniotic fluid in the gestational sac through the flow passage part.

13. The catheter unit according to claim 1, wherein the the double-pipe structure comprises:

a catheter body part (20$d$) implemented as a hollow type;

a catheter inner body part (20-2$d$) formed as a hollow type located in the catheter body part (20$d$); and a plurality of support bridge (20-3$d$) for connecting the catheter inner body part (20-2$d$) and the catheter body part (20$d$), the plurality of support bridge (20-3$d$) disposed spaced apart from each other at uniform intervals along a lengthwise direction of the catheter body part (20$d$).

14. The catheter unit according to claim 13, wherein the catheter further comprises:

a catheter injection through-hole (22$d$) formed at a space between the catheter body part (20$d$) and the catheter inner body part (20-2$d$); and a catheter suction through-hole (23$d$) formed at the internal space defined by the catheter inner body part (20-2$d$), and wherein the catheter injection through-hole (22$d$) and the catheter suction through-hole (23$d$) are disposed concentrically.

15. The catheter unit according to claim 14, wherein the catheter includes a catheter body branched part (20-4$d$) branched off from the catheter body part (20$d$) in a "Y" shape, and wherein the catheter body branched part (20-4$d$) includes a catheter injection-extending through-hole (22-2$d$) formed therein and connected to the catheter injection through-hole (22$d$).

16. The catheter unit according to claim 14, wherein the at least one flow passage part is connected to any one of the catheter injection through-hole (22$d$) and the catheter suction through-hole (23$d$).

17. The catheter unit according to claim 1, wherein:

the double-pipe structure includes an inner pipe portion, an outer pipe portion and a bridge portion; and the inner pipe portion is disposed inside the outer pipe portion, such that the inner pipe portion is supported by the bridge portion which connects an outer surface of the inner pipe portion and an inner surface of the outer pipe portion.

18. The catheter unit according to claim 1, wherein:

the flow passage is formed such that liquid introduced into the catheter through the one end of the catheter flows in a first direction from the one end to the other end, and liquid introduced into the catheter through the other end of the catheter flows in a second direction from the other end to the one end.

19. The catheter unit according to claim 1, wherein the direction control line is implemented in the catheter guide as a plurality of electrical signal lines, and wherein each of the electrical signal lines is connected to at least one of the direction control units.

20. The catheter unit according to claim 19, wherein the direction control units include a shape memory alloy so as to be deformed into a preset shape when predetermined electrical signals are applied to the direction control units through the direction control lines.

21. The catheter unit according to claim 19, wherein, when predetermined electrical signals are applied to the direction control units through the direction control lines, the direction control units generate heat and are deformed into a preset shape.

* * * * *